(12) United States Patent
Crawford et al.

(10) Patent No.: US 9,931,428 B2
(45) Date of Patent: Apr. 3, 2018

(54) OPHTHALMIC COMPOSITIONS

(75) Inventors: Francesca Crawford, Cambridge (GB);
Philip Gunning, Cambridge (GB);
Howard Thomas, Kimbolton (GB)

(73) Assignee: ORALDENT LIMITED, Kimbolton, Cambridgesh (GB)

( * ) Notice: Subject to any disclaimer, the term of this patent is extended or adjusted under 35 U.S.C. 154(b) by 203 days.

(21) Appl. No.: 14/125,427

(22) PCT Filed: Jun. 13, 2011

(86) PCT No.: PCT/GB2011/051105
§ 371 (c)(1),
(2), (4) Date: Mar. 14, 2014

(87) PCT Pub. No.: WO2012/172274
PCT Pub. Date: Dec. 20, 2012

(65) Prior Publication Data
US 2014/0186474 A1 Jul. 3, 2014

(51) Int. Cl.
| A61K 36/752 | (2006.01) |
| A61L 12/14 | (2006.01) |
| A61K 31/353 | (2006.01) |
| A01N 65/36 | (2009.01) |
| C11D 3/00 | (2006.01) |
| C11D 7/26 | (2006.01) |

(52) U.S. Cl.
CPC ............ *A61L 12/14* (2013.01); *A01N 65/36* (2013.01); *A61K 31/353* (2013.01); *A61K 36/752* (2013.01); *C11D 3/0078* (2013.01); *C11D 7/267* (2013.01)

(58) Field of Classification Search
None
See application file for complete search history.

(56) References Cited

U.S. PATENT DOCUMENTS

| 6,706,256 B2 * | 3/2004 | Lawlor ............... A23G 3/36 424/440 |
| 2003/0086986 A1 * | 5/2003 | Bruijn .............. A61K 9/0048 424/729 |
| 2007/0207116 A1 | 9/2007 | Brown |
| 2010/0055053 A1 * | 3/2010 | Ripley .............. A61K 8/365 424/49 |
| 2010/0209536 A1 | 8/2010 | Weiss |
| 2010/0209539 A1 * | 8/2010 | Renneberg .......... A61K 36/752 424/660 |

FOREIGN PATENT DOCUMENTS

| EP | EP 2198862 A1 | 6/2010 |
| JP | 2009/073952 A | 4/2009 |
| WO | WO 97/31658 A1 | 9/1997 |
| WO | WO 02/20028 A3 | 2/2003 |
| WO | WO 2007/125731 A1 | 11/2007 |
| WO | WO 2008/009958 A1 | 1/2008 |
| WO | WO 2008/061536 A1 | 5/2008 |

OTHER PUBLICATIONS

Benavente-Garcia et al. Journal of Agricultural and Food Chemistry. 1997 vol. 45 No. 12 pp. 4505-4515.
Shiratori, Kenji, et al. "The Effects of Naringin and Naringenin on Endotoxin-induced Uveitis in Rats." Journal of Ocular Pharmacology & Therapeutics 2005 vol. 21 No. 4 pp. 298-304.
International Search Report PCT/GB2011/051105. dated Jun. 13, 2011.

* cited by examiner

*Primary Examiner* — Christopher R Tate
*Assistant Examiner* — Russell G Fiebig
(74) *Attorney, Agent, or Firm* — Lathrop Gage LLP; James H. Velema, Esq.

(57) ABSTRACT

The present invention relates to compositions and methods for eye and contact lens care. More particularly, the invention relates to ophthalmic compositions which contain at least one bioflavonoid component for ocular care, preserving ophthalmic solutions and/or disinfecting contact lenses.

11 Claims, 8 Drawing Sheets

Figure 8.

*Fusarium solani*

Figure 9.

*Fusarium solani*

US 9,931,428 B2

OPHTHALMIC COMPOSITIONS

RELATED APPLICATIONS

This application is a 35 U.S.C. §371 filing of International Application No. PCT/GB2011/051105, filed Jun. 13, 2011. The entire contents of which are incorporated herein by reference.

FIELD OF THE INVENTION

The present invention relates to compositions and methods for eye and contact lens care. More particularly, the invention relates to ophthalmic compositions which contain at least one bioflavonoid component for ocular care, preserving ophthalmic solutions and/or disinfecting contact lenses.

BACKGROUND OF THE INVENTION

Products for contact lens disinfection by chemical means are intended to reduce microbial contamination introduced during lens wear and removal, cleaning and storage and are required to contain antimicrobial agents capable of achieving this. Contact lenses are normally subject to a regimen of cleaning and contact lens disinfection between periods of wear. Aqueous solutions containing cleaning and/or disinfecting agents are commonly used for this purpose.

Many multi-purpose solutions that may be used to clean, disinfect, and wet contact lenses, followed by direct insertion into the eye, are available. Multi-purpose solutions must be strong enough to kill harmful microorganisms that may be present or grow on the lenses while being gentle enough to use on the eyes. Such a solution also must be compatible with the many contact lens materials in use, which includes rigid gas permeable, traditional soft hydrophilic lenses (both high and low water content) and silicone hydrogel lenses. Measures of contact lens compatibility include contact lens discoloration, physical parameter change, fragility, and uptake/release of solution components, especially antimicrobial agents. Contact lens care solutions, such as a multi-purpose solutions (MPSs) (sometimes called "all-in-one" solutions), attempt to balance cleaning and disinfection ability with safety and comfort on the eyes. The addition of more effective disinfecting agents usually has the effect of reducing contact lens material compatibility or ocular comfort of the solution. One way to achieve additional material compatibility and comfort is to reduce the amount of disinfecting agent. However, conventional knowledge dictates that this results in lower antimicrobial efficacy.

There is need for an ophthalmic antimicrobial that exhibits broad and strong biocidal efficacy while causing minimal ocular irritation or user discomfort. The disclosed compositions and methods address this need by providing an aqueous soluble complex containing at least one bioflavonoid.

Certain compositions comprising bioflavonoids having some anti-bacterial and anti-viral activity are known.

US2007/0207116, whose entire disclosure is herein incorporated by reference, relates to ophthalmic compositions comprising at least one antioxidant agent chosen from a carotenoid, glutathione, reduced glutathione, glutathione enhancers, a lipoic acid, a bioflavonoid, an oleanoic acid, ascorbyl palmitate, aloe vera extract, an omega-6 fatty acid, melatonin, and vitamin E acetate.

WO2008/061536, whose entire disclosure is herein incorporated by reference, relates to compositions comprising at least one bioflavonoid for the treatment or amelioration of a disease or disorder of the eye and/or the adnexa of the eye in an animal subject, including a human being.

WO02/20028, whose entire disclosure is herein incorporated by reference, relates to compositions and methods for preventing eye disorders by protecting cells from damaging effects of free radicals. The methods involves administering to a subject a composition comprising alpha-lipoic acid, natural mixed tocopherols, vitamin C, *citrus* bioflavonoids, pine bark extract, lutein, natural mixed carotenoids and vitamin A.

WO2008/009958, whose entire disclosure is herein incorporated by reference, relates to an oral composition having a pH in the range of from 3 to 8.5, comprising: (a) in the range of from 0.1% to <10% w/w (based on the total weight of the oral composition) of a stock solution comprising a mixture of bioflavonoids and fruit acids or salts thereof; and (b) water; and, optionally, (c) a pharmaceutically acceptable carrier therefor.

EP2198862, whose entire disclosure is herein incorporated by reference, relates to bioflavonoids for the use in the treatment of parasitic infection.

SUMMARY OF THE DISCLOSURE

The present invention relates to compositions and methods for eye and contact lens care. In the first aspect of the invention, there is provided an aqueous antimicrobial contact lens storage and/or disinfection composition comprising at least one bioflavonoid.

According to a second aspect of the invention, there is provided an aqueous antimicrobial contact lens storage and/or disinfection composition comprising at least one bioflavonoid which comprises an ophthalmic adjuvant component selected from the group consisting of: a buffer; a viscosity-inducing component and a tonicity component comprising about 0.1% to 1.0% of sodium chloride; or a combination thereof.

According to a third aspect of the invention, there is provided a method of storing or disinfecting a contact lens which comprises bringing said contact lens into contact with a said composition above, preferably for at least 1 hour.

The contact lens is disinfected with respect to actual or potential colonisation by one or more microorganisms selected from *Acanthamoeba* sp, *Aspergillus niger*, *Bacillus cereus*, *Clostridium difficile*, *Staphylococcus aureus*, *Pseudomonas aeruginosa*, *Staphylococcus epidermidis*, methicillin resistant *Staphylococcus aureus* (MRSA) and *Fusarium solani*. With respect to actual or potential colonisation by the microorganism *Acanthamoeba*, the disinfection affects trophozoites and/or cysts.

According to a fourth aspect of the invention, there is provided the use of a composition according to the first aspect of the invention for storing or disinfecting a contact lens, preferably for a least 1 hour, for example for at least 6 hours, for example overnight. Storage will typically be at ambient temperature, e.g. a temperature of 18 to 24° C. e.g. around 20° C.

According to a fifth aspect of the invention, there is provided the use of at least one bioflavonoid as a preservative for an ophthalmic composition.

According to a sixth aspect of the invention, there is provided a method of preserving an ophthalmic aqueous composition which comprises use of at least one bioflavonoid in said ophthalmic composition as a preservative.

The use or method according to the fifth and sixth aspects of the invention for preserving is preferably with respect to actual or potential colonisation by one or more microorganisms selected from *Acanthamoeba* sp, *Aspergillus niger, Bacillus cereus, Clostridium difficile, Staphylococcus aureus, Pseudomonas aeruginosa, Staphylococcus epidermidis*, methicillin resistant *Staphylococcus aureus* (MRSA) and *Fusarium solani*. With respect to actual or potential colonisation by the microorganism *Acanthamoeba*, the disinfection affects both trophozoites and/or cysts According to a seventh aspect of the invention, there is provided an aqueous composition comprising at least one bioflavonoid for use in the treatment or prevention of infection or colonisation of the eye by one or more microorganisms selected from *Acanthamoeba* sp, *Aspergillus niger, Bacillus cereus, Clostridium difficile, Staphylococcus aureus, Pseudomonas aeruginosa, Staphylococcus epidermidis*, methicillin resistant *Staphylococcus aureus* (MRSA) and *Fusarium solani*.

According to the eighth aspect of the invention, there is provided a method of treating or preventing infection or colonisation of the eye of a subject by one or more microorganisms selected from *Acanthamoeba* sp, *Aspergillus niger, Bacillus cereus, Clostridium difficile, Staphylococcus aureus, Pseudomonas aeruginosa, Staphylococcus epidermidis*, methicillin resistant *Staphylococcus aureus* (MRSA) and *Fusarium solani* which comprises administering to said subject a composition comprising at least one bioflavonoid. With respect to infection or colonisation by the microorganism *Acanthamoeba*, the treatment or prevention affects both trophozoites and/or cysts. There is also provided a method for reducing the populations of the trophozoites and/or cysts forms of *Acanthamoeba* sp. comprising administering to said subject a composition comprising at least one bioflavonoid.

DESCRIPTION OF FIGURES

Figures 8, 9:
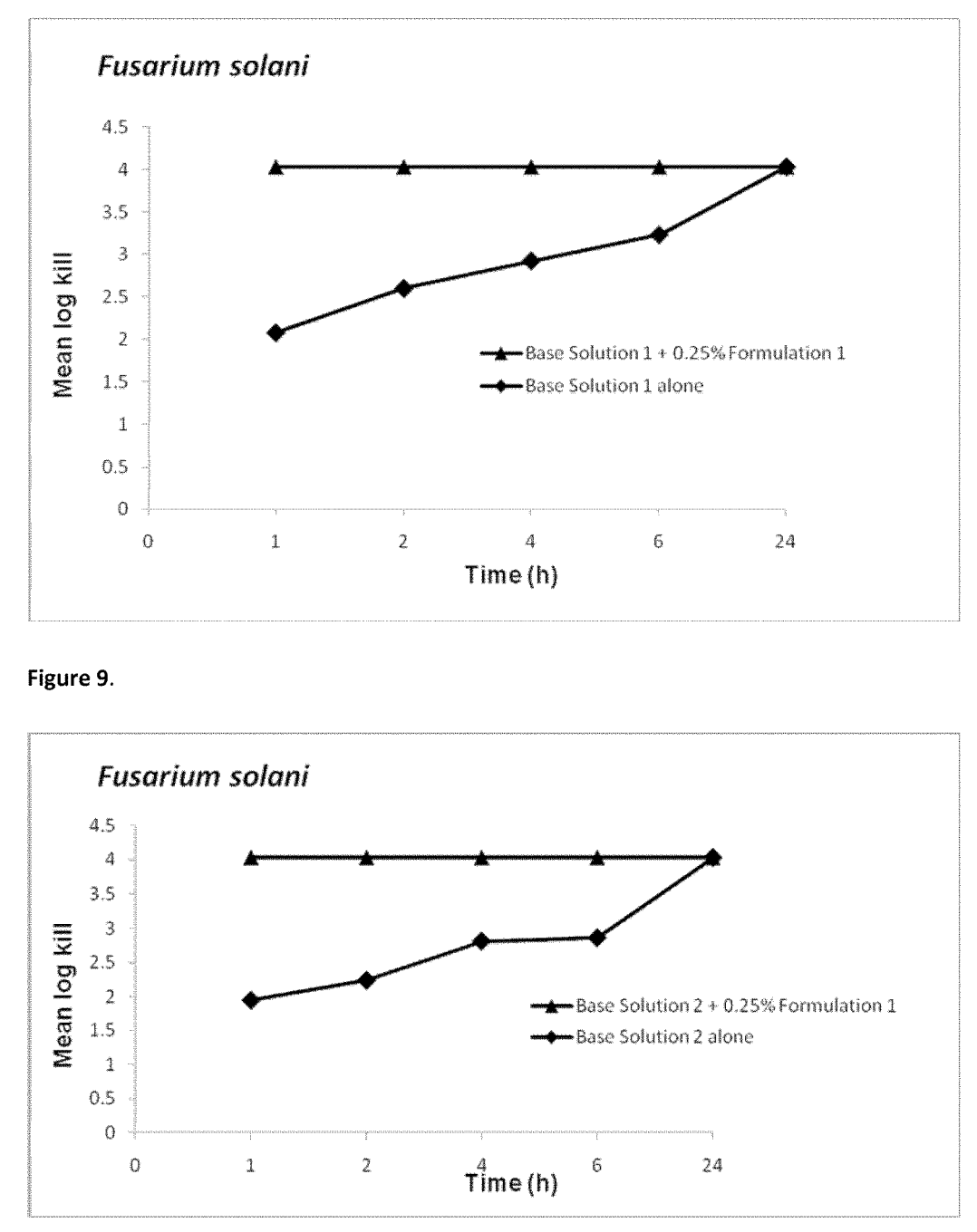

FIG. 8. The disinfecting effect of the addition of Formulation 1 to Contact Lens Solution 1 on a population of *Fusarium solani*

FIG. 9. The disinfecting effect of the addition of Formulation 1 to Contact Lens Solution 2 on a population of *Fusarium solani*

DETAILED DESCRIPTION OF THE INVENTION

Figure 1:
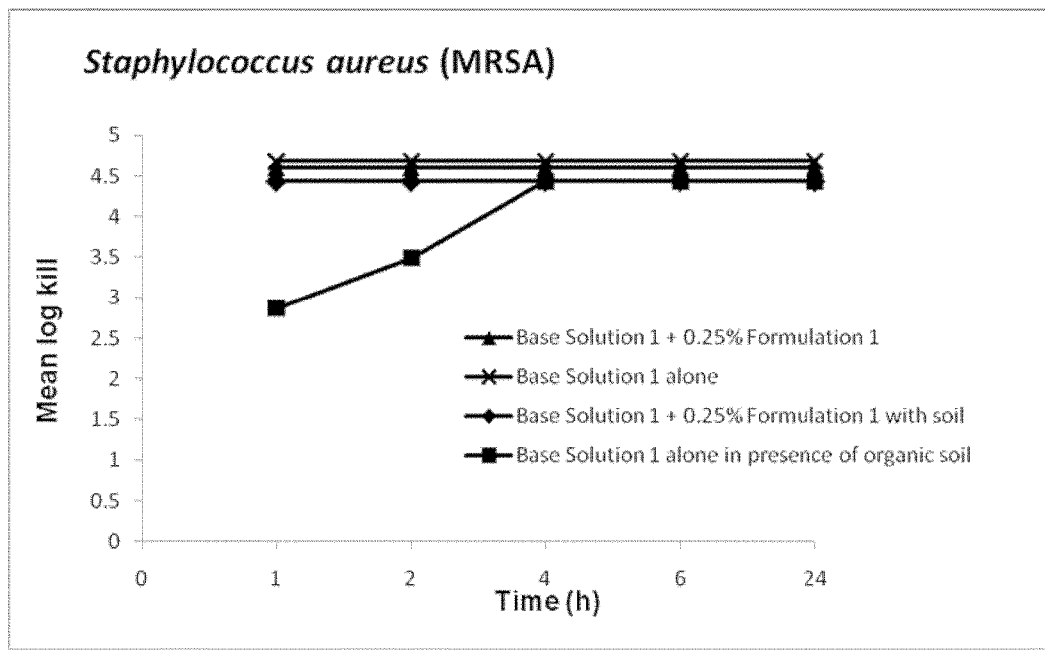
FIG. 1. The disinfecting effect of the addition of Formulation 1 to Contact Lens Solution 1 on a population of methicillin-resistant *Staphylococcus aureus* (MRSA) in the presence or absence of organic soil.

The term "bioflavonoid" refers to a class of plant secondary metabolites having a polyhydroxypolyphenol structure often as glycosides. The term covers flavonoids derived from the 2-phenylchromen-4-one (2-phenyl-1,4-benzopyrone) structure (examples: quercetin, rutin), isoflavonoids, derived from the 3-phenylchromen-4-one (3-phenyl-1,4-benzopyrone) structure, neoflavonoids, derived from the 4-phenylcoumarine (4-phenyl-1,2-benzopyrone) structure, flavanones, derived from 2,3-dihydro-2-phenylchromen-4-one (examples hesperidin, naringin) and flavan-3-ols (catechins)

The at least one bioflavonoid of any of the preceding aspects of the inventions is preferably derived from fruits of *Citrus* species, most preferably the at least one bioflavonoid is derived from the pith of immature bitter oranges, *Citrus aurantium* L The at least one bioflavonoid from any of the preceding aspects of the inventions can be one of a complex mixture of bioflavonoids. For example, a mixture of bioflavonoids obtained from the fruits of *Citrus aurantium* contains at least nine flavonoids. The mixture of flavonoids may aptly contain one or more (or 2 or 3 or 4 or 5 or 6 or 7 or 8 or more, or all 9) of neoeriocitrin, isonaringin, naringin, hesperidin, neohesperidin, neodiosmin, naringenin, poncirin and rhiofolin. Such a mixture of flavonoids can be obtained from bitter oranges, see for example WO2008/009956 the contents of which are herein incorporated by reference in their entirety.

It is presently believed that mixtures of such flavonoids have advantages over the use of a single flavonoid. It is particularly advantageous that extract of bitter oranges may be employed without the need for isolating individual flavonoids if desired.

One or more bioflavonoids may, however, be partially or completely purified, if desired, with respect to the substances with which they are naturally associated (including other bioflavonoids).

Aptly the mixture of flavonoids will comprise at least 25%, more suitably at least 40% and preferably at least 50% of naringin. More aptly the mixture will contain up to 65% of naringin. Aptly the mixture of flavonoids will comprise at least 15%, more suitably at least 20% and preferably at least 25% of neohesperidin. More aptly the mixture will contain up to 35% of neohesperidin. In a favoured form the mixture will contain at least 75% of neohesperidin and naringin. The aforementioned % values are w/w.

Aptly, the mixture of bioflavonoids will be water soluble.

Aptly, the bioflavonoid mixture comprises water-soluble bioflavonoids in association with biomass resulting from the extraction process; accordingly, the bioflavonoid mixture may be associated with up to 40-70% w/w, preferably about 55% w/w, biomass (based on the weight of the bioflavonoid mixture). The flavonoids are preferably glycosides, especially those selected from neoeriocitrin, isonaringin, naringin, hesperidin, neohesperidin, neodiosmin, naringenin, poncirin and rhiofolin, and more preferably each of these is present in the mixture. Especially preferred is when the major part of the bioflavonoid mixture (i.e. more than 50%) comprises naringin and neohesperidin, such as when these comprise in excess of 75% of the bioflavonoid component (excluding biomass). Suitably, other bioflavonoids (such as flavonol, chrysin, hesperetin) are substantially absent from the bioflavonoid mixture and the bioflavonoid component therefore consists essentially of the water-soluble bioflavonoids listed hereinabove, although trace amounts of other bioflavonoids may be present.

A suitable source of such a water-soluble bioflavonoid mixture is herein referred to as 'HPLC 45', of which about 45% w/w (of the total composition of HPLC 45) comprises such bioflavonoids, with the balance (about 55%) comprising biomass such as pectins, sugars and minor organic acids. As stated above, especially preferred is when the major part of the bioflavonoid mixture comprises naringin and neohesperidin, such as when these comprise in excess of 35% of the bioflavonoid component in a mixture with biomass such as HPLC 45. WO2008/009958, the contents of which are herein incorporated in their entirety by reference, describes the process for the production of HPLC45. The following table gives a typical composition of HPLC 45.

| Constituent | % w/w |
| --- | --- |
| Neoeriocitrin | 1.1 |
| Isonaringin | 1.2 |
| Naringin | 23.4 |
| Hesperidin | 1.4 |
| Neohesperidin | 12.5 |
| Neodiosmin | 1.4 |
| Naringenin | 1.5 |
| Poncirin | 2.0 |
| Rhiofolin | 0.5 |
| Total bioflavonoid content | 45% |

The HPLC 45 is available from Exquim (the food arm of Grupo Ferrer) as *Citrus* Bioflavonoid Complex 45% HPLC.

Another suitable source of water-soluble bioflavonoids is a green tea extract (an extract of *Camellia sinensis*). Typically the extract contains the bioflavonoids epigallocatechin gallate, epigallocatechin, epicatechin gallate and epicatechin, of which, epigallocatechin gallate accounts for more than 40% w/w of the total content. Other components include three further flavonoids, kaempferol, quercetin, and myricetin.

Another example of a suitable source of water-soluble bioflavonoids is an extract of gingko (*Gingko biloba*) that contains approximately 24% flavonoids, consisting of 33 identified bioflavonoids.

In some embodiments it may be desirable that the composition containing one or more bioflavonoids of the present invention further comprises fruit acids. As noted in the Examples, presence of fruit acids in the composition can enhance anti-microbial activity. Examples of fruit acids include malic, ascorbic, citric and tartaric acid optionally in the form of a salt. For example ascorbic acid may be employed as choline ascorbate. Fruit acids, if present may be included at a concentration of 0.0001 to 1% w/v.

Contact Lens Storage/Sterilisation Applications

Compositions according to the invention for use in contact lens storage and sterilisation will typically contain bioflavonoids at a concentration of 0.000001 to 0.04% w/v. Contact lens storage and sterilisation solutions typically contain tonicity modifiers e.g. are based on physiological saline (e.g. NaCl 0.9% w/v in water) and can contain other components. Additional preservatives such as polyquarternium-1, myristamidopropyl dimethylamine, polyaminopropyl biguanide and polyhexamethylene biguanide can be included e.g. at an amount of 0.000005-0.001% w/v. although preferably they are not included. Further components that may desirably be present include viscosity enhancing agents such as hydroxypropylmethyl cellulose or a carbomer e.g. at an amount of 0.001-0.1% w/v. Surfactants can be included such as a poloxomer, i.e poloxamine or poloxomer 407, Tetronic 1304 or Surfac APG PC at an amount 0.001-0.1% w/v. Chelating agents such as EDTA, edentate disodium or nonanoylethylenediaminetriacetic acid can be included. Wetting agents such as propylene glycol, glycerol (glycerin) or hydroxyalkylphosphonate may also be used. Compositions for use in storing and sterilising contact lenses may also be suitable for use in wetting contact lens for insertion in the eye (i.e. are all-in-one solutions). Certain of the aforementioned additional components are more suitable when the composition is intended for contact lens wetting. The pH of sterilisation solutions is typically between 7.0 and 7.4. for maximum compatibility with the eye, though a pH from 5 to 8 can be tolerated. pH can be adjusted as necessary by addition of acid or base. Typically a buffer system, for example a buffer system based on citrate and/or borate and/or phosphate, such as a citric/borate, a borate or a citric/phosphate buffer, will be employed to maintain the pH range. Choline hydroxide might also be added.

Contact lens sterilisation solutions can either be provided ready made up with bioflavonoids or else can be provided as a kit such that the bioflavonoid is supplied as a concentration for dilution into other components of the solution at the time of use.

Ophthalmic Solution Preservation Applications

Ophthalmic solutions typically contain tonicity modifiers e.g. are based on physiological saline (e.g. NaCl 0.9% w/v in water) and can contain other components. Components may be included as mentioned above under "contact lens applications". Other components may be included according to the purpose e.g. pharmaceutically active components (anti-allergic active ingredients such as mast cell release inhibitors, anti-histamines etc) can be included. Ophthalmic solutions can either be provided ready made up with bioflavonoids or else can be provided as a kit such that the bioflavonoid is supplied as a concentration for dilution into other components of the solution at the time of use. Bioflavonoid concentration in the final ophthalmic solution is typically 0.000001 to 0.4% w/v.

Pharmaceutical Compositions for Treatment of Ocular Infection

For treatment of ocular infection, compositions will typically contain bioflavonoids at a concentration of 0.00001 to 0.4% w/v. Other components that may be present in the composition including buffers, tonicity modifiers, viscosity modifying agents and surfactants as mentioned above under "contact lens applications". The pH of such compositions will typically be from 5.5 to 8.0 e.g. 7.0 to 7.4.

For the treatment for ocular infection, typically the compositions may be applied up to 4 times a day, preferably 2 times a day, most preferably once a day. Aptly, the treatment will consist of the application of between one drops and twelve drops equating to about 0.5 ml at each dose period, or in the case of a gel formulation the application of a 'pea size' amount at each dose period.

General Matters

The compositions of any of the aspects of the invention can be suitably packaged in glass or plastic containers of suitable size, preferably in plastic containers. Examples of the types of suitable plastic may be high density polyethylene (HDPE), low density polyethylene (LDPE), polypropylene (PP) and polyethylene terephthalate (PET). The size of the container will depend on the application. For example, contact lenses may be packaged in sizes of 60 ml, 330 ml, 600 ml and for example anti-microbial eye-drops may be packaged in sizes of 0.5 ml up to 30 ml.

Compositions for ophthalmic use including contact lens applications are typically provided as sterile formulations. Sterilisation may be either by aseptic filling into sterilised containers, or by terminal sterilisation after filling either by the use of heat (autoclaving) or irradiation.

The present invention will now be illustrated by the following examples.

Example 1—Preparation of Stock Solutions a) Preparation of Citrus Bioflavonoid Complex The pith of immature, bitter oranges (Citrus aurantium) are milled and then crushed in water or water/ethanol. The resulting mixture is filtered to leave a water-soluble biomass, which is retained, and an insoluble biomass, which is discarded. The water-soluble biomass is then subjected to concentration and fine filtration to afford the water soluble bioflavonoids. The solution is then concentrated and vacuum dried to leave a brown, hygroscopic powder of Citrus Bioflavonoid Complex (CBC). Citrus Bioflavonoid Complex is also commercially available, for example from Exquim SA, Ferrer Group. Typically Citrus Bioflavonoid Complex contains around 45% bioflavonoids, with naringin and neohesperidin being the major components. The non-bioflavonoid components are typically pectins 10-15% w/w, proteins 10-15% and carbohydrates 5-6%.

b) Composition and Preparation of Formulations 1, 2, 3 and 4

The compositions of Formulations 1, 2, 3 and 4 are given in Table 1. To prepare a stock solution, demineralised water is added to a blender and heated to 50° C. The glycerin and choline ascorbate (if specified) is added while mixing. The solution is blended for 30 minutes, then Citrus Bioflavonoid Complex, citric acid, malic acid, ascorbic acid (if specified) and surfactant (if specified) are added whilst mixing. The product is then transferred to suitable containers and quality controlled.

TABLE 1

Constituents of Formulations 1, 2, 3 and 4

| Constituent | Formula 1 % w/w | Formula 2 % w/w | Formula 3 % w/w | Formula 4 % w/w |
|---|---|---|---|---|
| Citrus Bioflavonoid Complex | 3.3 | 3.3 | 3.25 | 3.25$ |

TABLE 1-continued

Constituents of Formulations 1, 2, 3 and 4

| Constituent | Formula 1 % w/w | Formula 2 % w/w | Formula 3 % w/w | Formula 4 % w/w |
|---|---|---|---|---|
| Malic acid | 4.5 | 4.5 | 8.75 | 8.75 |
| Citric acid | 4.5 | 4.5 | 8.75 | 8.75 |
| Ascorbic acid | 1.5 | — | — | — |
| Choline ascorbate | — | 6.0 | 4.0 | 4.0 |
| Glycerin | 7.5 | — | 0.83 | 0.83 |
| Berol LFG 61¶ | — | 13.3 | — | — |
| Propylene glycol | — | 7.5 | — | — |
| Surfac APG PC‡ | — | — | 3.0 | 3.0 |
| Water | 78.6 | 60.9 | 71.42 | 71.42 |
| pH | 1.5 to 1.75 | 1.5 to 1.75 | 2.2 | 2.39 |
| Total bioflavonoid content (ppm) | 14850 | 14850 | 14625 | 20000 |

¶Berol LFG 61, an alkoxylate surfactant is a combination of alkyl glucoside and ethoxylate surfactants
‡Surfac APG PC, an alkyl polyglucoside, is a mild, naturally derived non-ionic surfactant
$Flavonoid content = 61%

Example 2—Quantitative Suspension Test for the Evaluation of Bactericidal Activity Using the standard BS EN1276 Quantitative suspension test for the evaluation of bactericidal activity of chemical disinfectants and antiseptics used in food, industrial, domestic, and institutional areas, Formulations 1, 3 and 4 were tested after dilution with sterile hard water and shown to be effective against a number of bacteria under 'dirty conditions', i.e. in the presence of 0.3% w/v bovine serum albumin. Tables 2, 3 and 4 shows the microbial reduction afforded by Formulation 1, 3 and 4 respectively against the test organisms

TABLE 2

Effect of Formulation 1 on microorganisms using test EN 1276 under dirty conditions

| Test organism | Concentration (% v/v) | Bioflavonoid concentration (ppm) | Microbial reduction |
|---|---|---|---|
| Campylobacter jejuni NCTC 11322 | 0.2 | 29.70 | $3.26 \times 10^5$ |
| Enterococcus faecalis NCTC 8213 | 0.60 | 89.10 | $>1.32 \times 10^6$ |
| Enterococcus hirae ATCC 8043 | 0.20 | 29.70 | $>2.29 \times 10^6$ |
| Escherichia coli NCTC 10418 | 0.20 | 29.70 | $>4.05 \times 10^6$ |
| Lactobacillus acidophilus ATCC 4356 | 0.20 | 29.70 | $1.17 \times 10^5$ |
| Legionella pneumophila NCTC 11192 | 0.60 | 89.10 | ¥$1.90 \times 10^4$ |
| Mycobacterium fortuitum NCTC 8573 | 0.60 | 89.10 | ¥$9.15 \times 10^3$ |
| Pseudomonas aeruginosa ATCC 15442 | 0.20 | 29.70 | $1.9 \times 10^6$ |
| Staphylococcus aureus NCTC 6571 | 0.20 | 29.70 | $>1.34 \times 10^6$ |
| Vibro parahaemolyticus ATTC 17802 | 0.20 | 29.70 | $3.50 \times 10^5$ |

¥bacterial activity in 15 minutes at 20° C. under dirty conditions

TABLE 3

Effect of Formulation 3 on microorganisms using test EN 1276 under dirty conditions

| Test organism | Conc (% v/v) | Bioflavonoid concentration (ppm) | Microbial reduction |
|---|---|---|---|
| Bacillus subtillus 10262 | 1 | 146.25 | $1.34 \times 10^5$ |
| Enterococcus hirae ATCC 8043 | 0.2 | 29.25 | $>4.40 \times 10^6$ |
| Escherichia coli NCTC 10418 | 0.2 | 29.25 | $>3.00 \times 10^6$ |
| Pseudomonas aeruginosa ATCC 15442 | 0.2 | 29.25 | $>2.40 \times 10^6$ |
| Staphylococcus aureus NCTC 6571 | 0.2 | 29.25 | $>5.58 \times 10^6$ |

TABLE 4

Effect of Formulation 4 on microorganisms using test EN 1276 under dirty conditions

| Test organism | Conc (% v/v) | Bioflavonoid concentration (ppm) | Microbial reduction |
|---|---|---|---|
| Enterococcus hirae ATCC 8043 | 1 | 169 | $>4.02 \times 10^6$ |
| Escherichia coli NCTC 10418 | 1 | 169 | $>5.49 \times 10^6$ |
| Pseudomonas aeruginosa ATCC 15442 | 1 | 169 | $>7.16 \times 10^4$ |
| Staphylococcus aureus NCTC 6571 | 1 | 169 | $>4.30 \times 10^6$ |

This example shows that even at concentrations of 30 ppm, the bioflavonoid compositions are effective at killing a range of bacteria species, and meet the requirements of BS EN1276 Quantitative suspension test for the evaluation of bactericidal activity of chemical disinfectants and antiseptics used in food, industrial, domestic, and institutional areas.

Example 3—Quantitative Suspension Test for the Evaluation of Sporicidal and Fungicidal Activity Using the standards BS EN 13704 Quantitative suspension test for the evaluation of sporicidal activity of chemical disinfectants used in food, industrial, domestic and institutional areas and BS EN 1650 Quantitative suspension test for the evaluation of fungicidal or yeasticidal activity of chemical disinfectants used in food, industrial, domestic and institutional areas, Formulation 1 was tested and shown to be effective against Bacillus cereus, two species of Clostridium sp. three fungal species and a yeast. Table 5 shows the microbial reduction afforded by Formulation 1 after dilution with sterile hard water against the test organisms under 'dirty conditions', i.e. in the presence of 0.3% w/v bovine serum albumin (Test EN 13704) or 5% w/v yeast suspension (Test EN 1650).

TABLE 5

Effect of Stock Solution 1 on microorganisms using test EN 13704 and EN 1650 under dirty conditions

| Test organism | Concentration (% v/v) | Bioflavonoid concentration (ppm) | Test[†] | Microbial reduction |
|---|---|---|---|---|
| Aspergillus niger NCPF 2275 | 1.0 | 146.3 | EN 1650 | $8.71 \times 10^3$ |
| Bacillus cereus ATCC 12826 | 0.5 | 73.1 | EN 13704 | $1.73 \times 10^3$ |
| Candida albicans NCPF 3179 | 1.0 | 146.3 | EN 1650 | $2.24 \times 10^4$ |
| Clostridium difficile ATCC 11437 | 0.40 | 58.5 | EN 13704 | $3.93 \times 10^3$ |
| Clostridium perfringens | 0.40 | 58.5 | EN 13704 | $1.08 \times 10^4$ |
| Penicillium digitatum | 1.50 | 219.4 | EN 1650 | $2.16 \times 10^6$ |
| Phytophthora ramorum | 0.50 | 73.1 | EN 1650 | $2.76 \times 10^4$ |

[†]30 minutes at 20° C. under dirty conditions

This example shows that at concentrations of 60-220 ppm, the bioflavonoid composition is effective at killing a range of fungal and yeast species, and meets the requirements of BS EN 13704 Quantitative suspension test for the evaluation of sporicidal activity of chemical disinfectants used in food, industrial, domestic and institutional areas and BS EN 1650 Quantitative suspension test for the evaluation of fungicidal or yeasticidal activity of chemical disinfectants used in food, industrial, domestic and institutional areas Example 4—Enhancement of Antibacterial Activity of Bioflavonoid Using Fruit Acids A study was undertaken comparing the activity of a mixture of bioflavonoid and a fruit acid against the individual components. Using the standard BS EN1276 Quantitative suspension test for the evaluation of bactericidal activity of chemical disinfectants and antiseptics used in food, industrial, domestic, and institutional areas, an aqueous solution of citric acid, an aqueous solution of Citrus Bioflavonoid Complex and a combination of citric acid and Citrus Bioflavonoid Complex was compared. Table 6 shows the activity of the three test samples against four bacteria.

TABLE 6

Effect of citric acid, citrus bioflavonoid complex and a combination of the two on microorganisms using test EN 1276 under dirty conditions

| Test organism | Test article | Microbial reduction |
|---|---|---|
| Bacillus subtillus 10262 | Citric acid | $2.29 \times 10^3$ |
| Bacillus subtillus 10262 | CBC | $6.46 \times 10^3$ |
| Bacillus subtillus 10262 | CBC + citric acid | $3.80 \times 10^5$ |
| Escherichia coli 11867 | Citric acid | $6.46 \times 10^2$ |
| Escherichia coli 11867 | CBC | $7.08 \times 10^3$ |
| Escherichia coli 11867 | CBC + citric acid | $9.55 \times 10^5$ |
| Pseudomonas aeruginosa ATCC 15442 | Citric acid | $2.69 \times 10^3$ |
| Pseudomonas aeruginosa ATCC 15442 | CBC | $1.95 \times 10^4$ |
| Pseudomonas aeruginosa ATCC 15442 | CBC + citric acid | $3.72 \times 10^6$ |
| Staphylococcus aureus NCTC 6571 | Citric acid | $3.02 \times 10^2$ |
| Staphylococcus aureus NCTC 6571 | CBC | $2.04 \times 10^2$ |
| Staphylococcus aureus NCTC 6571 | CBC + citric acid | $4.17 \times 10^5$ |

Table 6 shows that all three test samples showed antibacterial activity, with the combination having an enhanced effect.

Example 5—Effects of Formulation 4 on *Acanthamoeba polyphaga*

The purpose of the study is to evaluate the efficacy of Formulation 4 against the trophozoite form of the ocular pathogenic free-living amoeba *Acanthamoeba*. Contact lenses are normally subject to a regimen of cleaning and disinfection between periods of wear. Whilst it is a requirement that solutions for contact lens disinfection must be shown to have activity against bacteria and fungi, efficacy against the free-living amoeba *Acanthamoeba* is not presently a requirement of the international standard for testing contact lens care products. However, *Acanthamoeba* is a rare but serious ocular pathogen with up to 90% of cases reported in contact lens wearers.

The minimum trophozoite amoebicidal concentration (MTAC) and the minimum cysticidal concentration (MCC) of antimicrobial solutions against the ocular pathogenic free-living amoeba *Acanthamoeba polyphaga* was evaluated using the broth microdilution method.

Formulation 4 (1 ml) was diluted with saline (0.9% w/v, 8 ml), adjusted with 5 M NaOH to pH=7, made up to 10 ml with more saline, and filtered to afford a 10% dilution of the formulation (Test solution 1). This equates to 1.6 mg/ml of bioflavonoids. By the same method, a further sample that was adjusted to pH=5 was produced (Test solution 2).

Organism Preparation

*Acanthamoeba* Trophozoites

*Acanthamoeba polyphaga* (Ros) strain obtained from the laboratory culture collection was grown in Ac#6 medium at the appropriate temperature. Once confluent growth had occurred, the trophozoites were harvested and washed with ¼ strength Ringer's solution. The trophozoites concentration was adjusted to $2 \times 10^4$ trophozoites/ml using Ac#6 medium.

*Acanthamoeba* Cysts

*Acanthamoeba polyphaga* (Ros) strain obtained from the laboratory culture collection was grown in Ac#6 medium at the appropriate temperature. Once confluent growth had occurred, the trophozoites were harvested and washed with encystment medium. The trophozoites were re-suspended in encystment medium and incubated with shaking at the appropriate temperature for 5-7 days. The resulting cysts were harvested and washed with ¼ strength Ringer's solution. The cyst concentration was adjusted to $2 \times 10^4$ cyst/ml using ¼ strength Ringer's solution prior to use.

Preparation of Test and Control Samples

Each test solution was tested in triplicate against trophozoites or cysts prepared as detailed above. For trophozoite assays, Ac#6 medium was added to wells 2-12 of rows A, B, C, F, G and H of a 96-well flat bottomed microtitre plate. For cyst assays, ¼ strength Ringer's solution as added to wells 2-12 of rows A, B, C, F, G and H of a 96-well flat bottomed microtitre plate. The test solution 2 was added to wells A1, B1 and C1, and test solution 1 was added to wells F1, G1 and H1. Serial 2-fold dilutions of the test solutions across the microtitre plate from rows 2-11 were made. The dilution and concentration of bioflavonoids in each well is given in Table 7 below.

TABLE 7

|  | Well | | | | | | | | | |
| --- | --- | --- | --- | --- | --- | --- | --- | --- | --- | --- |
|  | 1 | 2 | 3 | 4 | 5 | 6 | 7 | 8 | 9 | 12 |
| Test solution dilution | 1:2 | 1:4 | 1:8 | 1:16 | 1:32 | 1:64 | 1:128 | 1:256 | 1.512 | Control |
| Test solution % v/v | 5 | 2.5 | 1.25 | 0.625 | 0.313 | 0.156 | 0.078 | 0.039 | 0.0195 |  |
| Bioflavonoid content (µg/ml) | 1000 | 500 | 250 | 125 | 62 | 31 | 15.5 | 7.75 | 3.85 | 0 |
| Test solution dilution | 1:2 | 1:4 | 1:8 | :16 | 1:32 | 1:64 | 1:128 | 1:256 | 1.512 | Control |
| Test solution % v/v | 5 | 2.5 | 1.25 | 0.625 | 0.313 | 0.156 | 0.078 | 0.039 | 0.0195 |  |
| Bioflavonoid content (µg/ml) | 1000 | 500 | 250 | 125 | 62 | 31 | 15.5 | 7.75 | 3.85 | 0 |
| Test solution dilution | 1:2 | 1:4 | 1:8 | 1:16 | 1:32 | 1:64 | 1:128 | 1:256 | 1.512 | Control |
| Test solution % v/v | 5 | 2.5 | 1.25 | 0.625 | 0.313 | 0.156 | 0.078 | 0.039 | 0.0195 |  |
| Bioflavonoid content (µg/ml) | 1000 | 500 | 250 | 125 | 62 | 31 | 15.5 | 7.75 | 3.85 | 0 |

The calibrated test organism was added to the test and control wells of rows A, B, C, F, G and H. The plates was covered and incubated at the appropriate temperature for 24 hours

*Acanthamoeba* Trophozoites

After 24 hours incubation, the wells were inspected using an inverted light microscope. The trophozoites in the test wells was compared to those in the control wells. The minimum trophozoite amoebicidal concentration (MTAC) for the test compound was determined as the lowest concentration of the test compound that gives complete lysis or degeneration of trophozoites.

*Acanthamoeba* Cysts

After 24 hours incubation, the contents of the wells were discarded. The Wells were refilled ¼ strength Ringer's solution and left for 15 minutes at room temperature. The washing procedure was repeated twice more. The wells were then filled with ¼ strength Ringer's solution containing live *Escherichia coli*. The plate was covered and incubated at the appropriate temperature for 14 days. The cysts in the test wells were compared to those in the control wells using an inverted light microscope. The minimum cysticidal concentration (MCC) was determined as the lowest concentration of the test compound that gave no excystment and trophozoite replication.

The results are shown in Table 8.

TABLE 8

Results of MTAC and MCC assays against *Acanthamoeba polyphaga* (Ros) trophozoites and cysts

| Bacteria Strain | Test solution 1 (pH 7) | | Test solution 2 (pH 5) | |
|---|---|---|---|---|
| | MTAC | MCC | MTAC | MCC |
| *Acanthamoeba polyphaga* (Ros) trophozoites | 0.313† | — | 0.313† | — |
| *Acanthamoeba polyphaga* (Ros) cysts | — | 0.625† | — | 0.625† |

†% v/v dilution of Formulation 4

Table 8 shows that both test solutions are effective at killing trophozoites and cysts of *Acanthamoeba polyphaga* (Ros), a rare but serious ocular pathogen.

Example 6—the In Vitro Susceptibility of Bacteria, Fungi and Yeasts

The in vitro susceptibility of bacteria, fungi and yeasts to antimicrobial compounds was assessed according to the procedures published by the Clinical and Laboratory Standards Institute (CLSI). The minimal inhibitory concentration (MIC) of antimicrobial solutions against bacterial and fungal ocular pathogens was evaluated using the broth microdilution method.

Formulation 4 (1 ml) was diluted with saline (0.9% w/v, 8 ml), adjusted with 5 M NaOH to pH=7, made up to 10 ml with more saline, and filtered to afford a 10% dilution of the formulation (Test solution 1). This equates to 1.6 mg/ml of bioflavonoids. By the same method, a further sample that was adjusted to pH=5 was produced (Test solution 2).

Organism Preparation

The organisms given in the Table 9 were incubated in the appropriate growth medium in accordance with the CLSI standard methods, then harvested and diluted to afford working stock suspensions in the ranges given in Table 10. The actual viable numbers were confirmed by making dilutions of the stock preparation and performing spiral plater counts.

TABLE 9

| Organism | Strain |
|---|---|
| Bacteria | |
| *Staphylococcus aureus* | (MRSA, blood stream infection) |
| *Staphylococcus epidermidis* | Tu3298 |

TABLE 9-continued

| Organism | Strain |
|---|---|
| *Bacillus cereus* | ATCC 14579 |
| *Pseudomonas aeruginosa* | (keratitis isolate) |
| Yeast | |
| *Candida albicans* | ATCC 10231 |
| Filamentous Fungi | |
| *Fusarium solani* | ATCC 36031 |
| *Aspergillus niger* | ATCC 16404 |

TABLE 10

| Organism | Working stock conc. |
|---|---|
| Bacteria | $4 \times 10^5$/ml-$1.6 \times 10^6$ CFU/ml |
| Fungi | $0.8 \times 10^4$/ml-$1 \times 10^5$/ml |
| Yeast | $1 \times 10^3$ CFU/ml-$5 \times 10^3$ CFU/ml |

Preparation of Test and Control Samples

Each test solution was tested in triplicate against each organism prepared as detailed above.

For bacterial tests, cation-adjusted Mueller-Hinton broth (CAMHB) and for yeast and fungi tests, Roswell Park Memorial Institute medium (RPMI-1640) was added to wells 2-12 of rows A, B, C, F, G and H of a 96-well round-bottomed microtitre plate, in accordance with the CLSI standard methods The test solution 2 was added to wells A1, B1 and C1, and test solution 1 was added to wells F1, G1 and H1. Serial 2-fold dilutions of the test solutions across the microtitre plate from rows 2-11 were made. The dilution and concentration of bioflavonoids in each well is given in the Table below.

TABLE 11

| | Well | | | | | | | | | |
|---|---|---|---|---|---|---|---|---|---|---|
| | 1 | 2 | 3 | 4 | 5 | 6 | 7 | 8 | 9 | 12 |
| Test solution dilution | 1:2 | 1:4 | 1:8 | 1:16 | 1:32 | 1:64 | 1:128 | 1:256 | 1.512 | Control |
| Test solution % v/v | 5 | 2.5 | 1.25 | 0.625 | 0.313 | 0.156 | 0.078 | 0.039 | 0.0195 | |
| Bioflavonoid content (μg/ml) | 1000 | 500 | 250 | 125 | 62 | 31 | 15.5 | 7.75 | 3.85 | 0 |

The calibrated test organism was added to the test and control wells of rows A, B, C, F, G and H. The plate was covered and incubated at the appropriate temperature for 24 hours (bacteria and yeast) or 48 hours (fungi).

The plates were inspected and the visual MIC recorded. The MIC is the lowest concentration of the solution that inhibits the visible growth of the organism. The wells containing the minimum inhibitory concentration were plated out along with the control wells on the appropriate solid media to quantify the levels of disinfection of the MIC test wells. In singlet, the test wells at the concentrations above the MIC were plated out to determine the minimal lethal concentration (MLC) for each microorganism. The MLC is defined as the lowest concentration of the solution required to kill the organism, i.e. no growth on solid media.

The results are shown in Tables 12 and 13.

TABLE 12

Results of MIC assays against bacteria

| Bacteria Strain | Formulation 4 (pH 7) MIC/MLC | Log kill* | Formulation 4 (pH 5) MIC/MLC | Log kill* |
|---|---|---|---|---|
| *Pseudomonas aeruginosa* (keratitis isolate) | 1.25† (2.50†)~ | 4.16 (8.38) | 1.25† (2.50†)~ | 3.86 (8.38) |
| *Staphylococcus epidermidis* (Tu3298) | 1.25† (2.5†) | 5.72 (8.57) | 2.5† (5.01†)~ | 6.07 (8.57) |
| *Staphylococcus aureus* (MRSA, blood culture isolate) | 0.156† (0.313†)~ | 6.82 (8.22) | 0.313† (0.625†)~ | 5.80 (8.22) |
| *Bacillus cereus* (ATCC 14579) | 0.625† (0.625†)~ | 7.41 (7.41) | 1.25† (1.25†)~ | 7.41 (7.41) |

*Compared with growth control wells
~Values in parentheses correspond to the minimal lethal concentration (MLC)
†% v/v dilution of Formulation 4

TABLE 13

Results of MIC assays against yeast and fungi

| Yeast and Fungi Strain | Formulation 4 (pH 7) MIC/MLC | Log kill* | Formulation 4 (pH 5) MIC/MLC | Log kill |
|---|---|---|---|---|
| *Candida albicans* (ATCC 10231) | 0.625† (1.25†)~ | 4.78 (5.86) | 0.625† (1.25†)~ | 5.56 (5.86) |
| *Fusarium solani* (ATCC 36031) [48 hours] | 0.313† (0.625†)~ | 4.19 (4.30) | 0.313† (0.313†)~ | 4.30 (4.30) |
| *Aspergillus niger* (ATCC 16404) [48 hours] | 0.156† (0.625†)~ | 3.06 (4.20) | 0.156† (0.313†)~ | 3.08 (4.20) |

*Compared with growth control wells
~Values in parentheses correspond to the minimal lethal concentration (MLC)
†% v/v dilution of Formulation 4

Tables 12 and 13 shows that both test solutions are effective at inhibiting the growth of bacteria, yeasts and fungi that are known to cause infections in the eye. There is a pH dependence with some organisms such that the test solution that was neutral was more effective than that test solution with pH=5.

Example 7—Addition of Formulation 1 to Contact Lens Solutions

The purpose of this study is to evaluate the ability of contact lens disinfectant solutions to reduce microbial populations. Solutions for contact lens disinfection are intended to reduce the microbial population introduced during lens use, removal, cleaning and storage. Efficacy of contact lens regimens can be determined through use of the FDA 1997 Premarket Notification (510K) Guidance Document for Contact Lens Care Products and ISO14729 Ophthalmic optics—Contact lens care products—Microbiological requirements and test methods for products and regimens for hygienic management of contact lenses. Existing contact lens solutions were spiked with various concentrations of Formulation 1 to determined whether an enhanced activity can be seen.

Samples

Test samples were provided as detailed in Table 14

TABLE 14

Test solutions

| Test solutions | Contents |
|---|---|
| Base solution 1 | Hydroxyalkylphosphonate (0.03%), poloxamine (1%), polyaminopropyl biguanide (0.0001%), boric acid, sodium borate, sodium chloride, edetate disodium |
| Base solution 1 + 0.25% Formulation 1 | as above with 0.0042% bioflavonoids |
| Base solution 1 + 0.10% Formulation 1 | as above with 0.0017% bioflavonoids |
| Base solution 1 + 0.05% Formulation 1 | as above with 0.0009% bioflavonoids |
| Base solution 1 in presence of 10% w/v organic soil | |
| Base solution 1 + 0.25% Formulation 1 in presence of 10% w/v organic soil | as above with 0.0042% bioflavonoids |
| Base solution 2 | TETRONIC ® 1304, nonanoyl ethylenediaminetriacetic acid, polyquarter-1 (0.001%), myristamidopropyldimethylamine (0.0005%) |
| Base solution 2 + 0.25% Formulation 1 | as above with 0.0042% bioflavonoids |
| Base solution 2 + 0.10% Formulation 1 | as above with 0.0017% bioflavonoids |
| Base solution 2 + 0.05% Formulation 1 | as above with 0.0009% bioflavonoids |
| Base solution 2 in presence of 10% w/v organic soil | |
| Base solution 2 + 0.25% Formulation 1 in presence of 10% w/v organic soil | as above with 0.0042% bioflavonoids |

% values in this table are v/v except where mentioned to the contrary

Organism Preparation

The organisms given in the Table 15 were incubated in the appropriate growth medium in accordance with the ISO14729 standard methods, then harvested and diluted to afford working stock suspensions in the ranges given in Table 16.

TABLE 15

| Organism | Strain |
|---|---|
| Bacteria | |
| *Staphylococcus aureus* | (MRSA, blood stream infection) |
| Yeast | |
| *Candida albicans* | ATCC 10231 |
| Filamentous Fungi | |
| *Fusarium solani* | ATCC 36031 |

*Staphylococcus aureus*, *Candida albicans* and *Fusarium solani*

TABLE 16

| Organism | Working stock conc. |
|---|---|
| Bacteria | $4.8 \times 10^5$ CFU/ml |
| Fungi | $1.1 \times 10^5$ CFU/ml |
| Yeast | $6.1 \times 10^5$ CFU/ml |

Preparation of Test and Control Samples

Each test solution was tested in triplicate against each organism prepared as detailed above.

Figure 2:
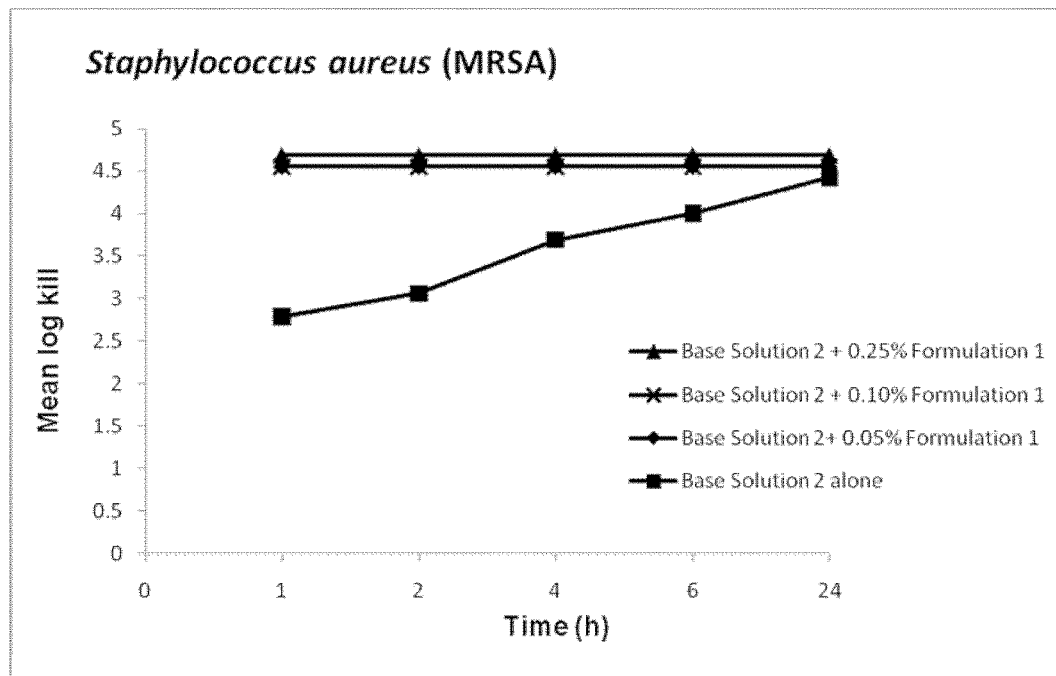
FIG. 2. The disinfecting effect of the addition of Formulation 1 to Contact Lens Solution 2 on a population of methicillin-resistant *Staphylococcus aureus* (MRSA).
Figure 3:
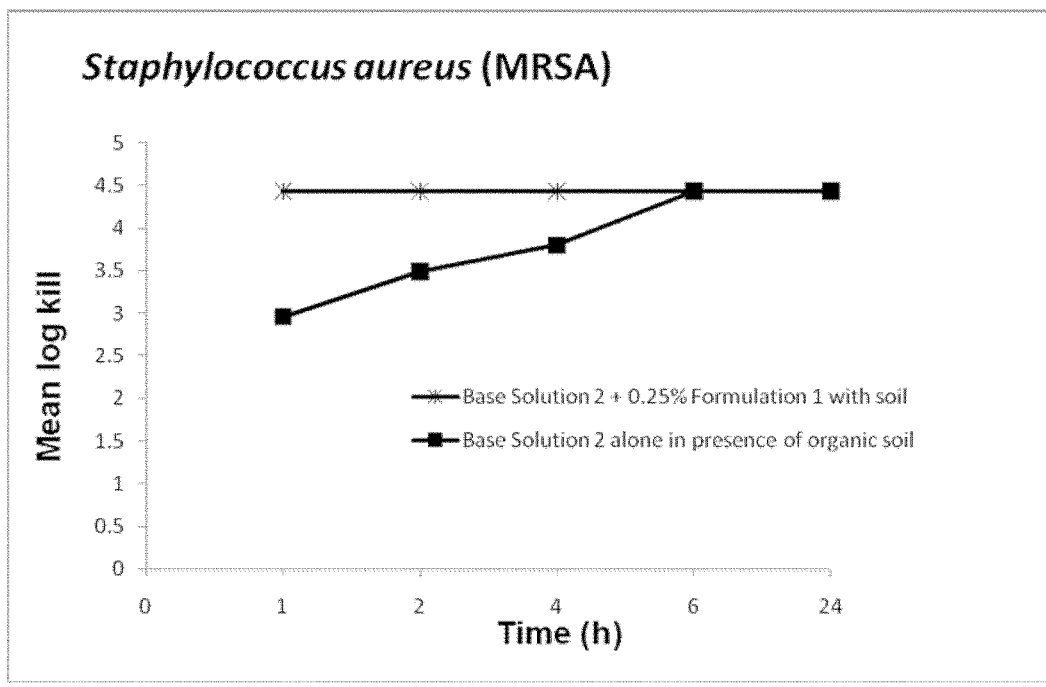
FIG. 3. The disinfecting effect of the addition of Formulation 1 to Contact Lens Solution 2 on a population of methicillin-resistant *Staphylococcus aureus* (MRSA) in the presence of organic soil.
Figure 4:
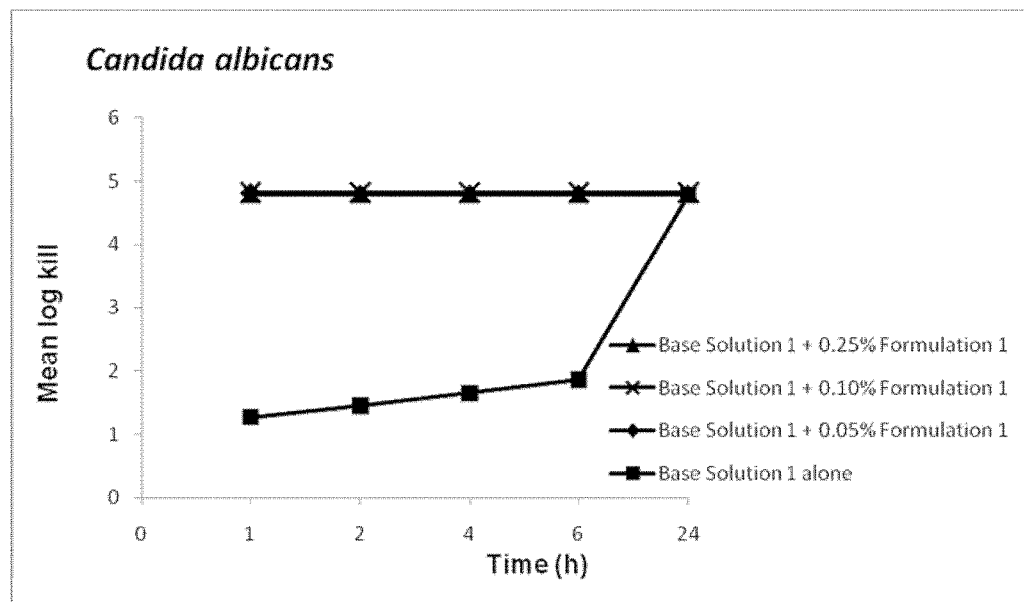
FIG. 4. The disinfecting effect of the addition of Formulation 1 to Contact Lens Solution 1 on a population of *Candida albicans*.
Figure 5:
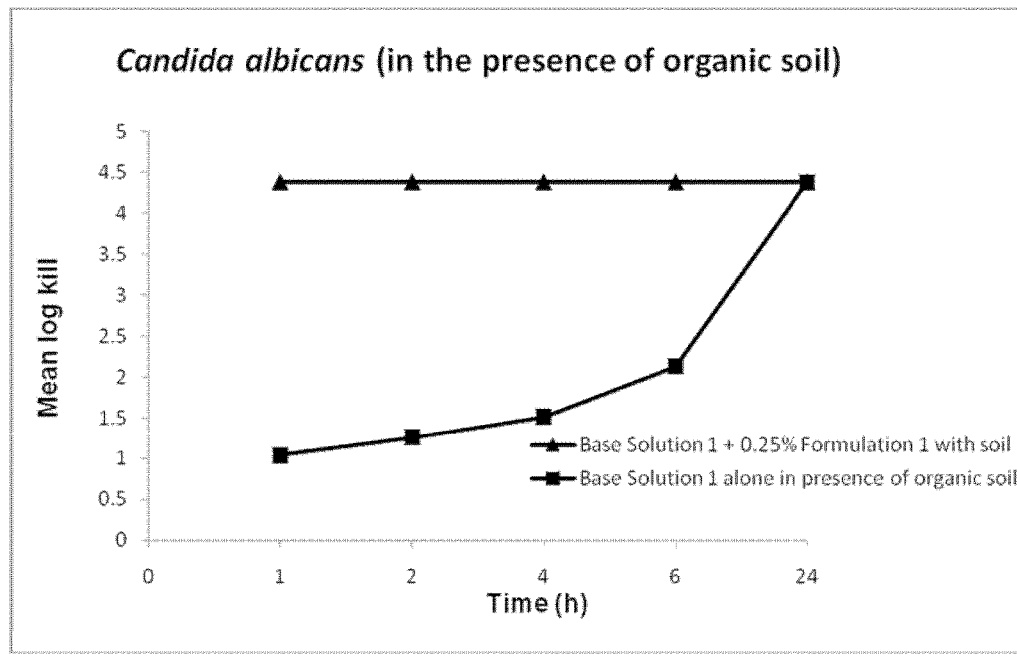
FIG. 5. The disinfecting effect of the addition of Formulation 1 to Contact Lens Solution 1 on a population of *Candida albicans* in the presence of organic soil.
Figure 6:
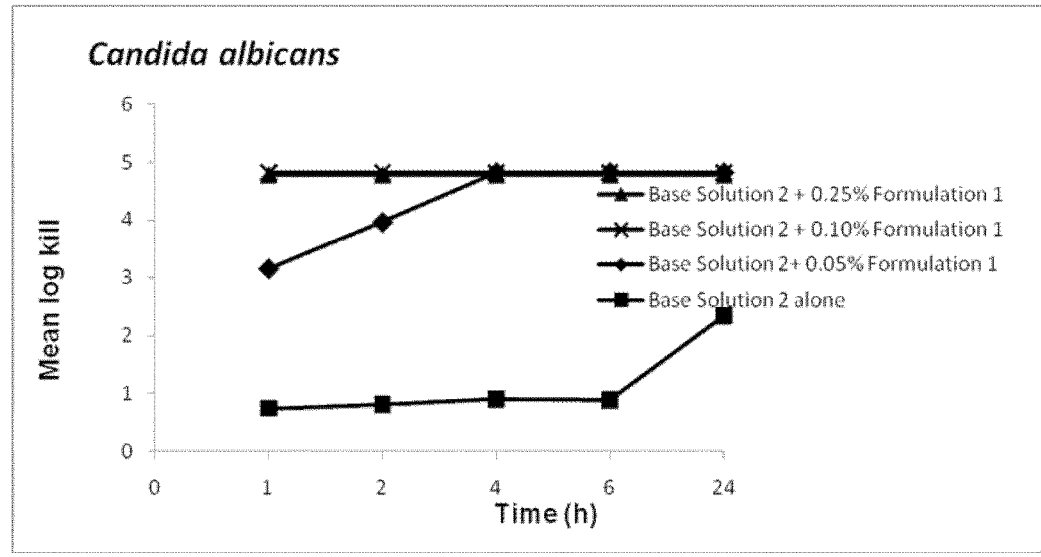
FIG. 6. The disinfecting effect of the addition of Formulation 1 to Contact Lens Solution 2 on a population of *Candida albicans*.
Figure 7:
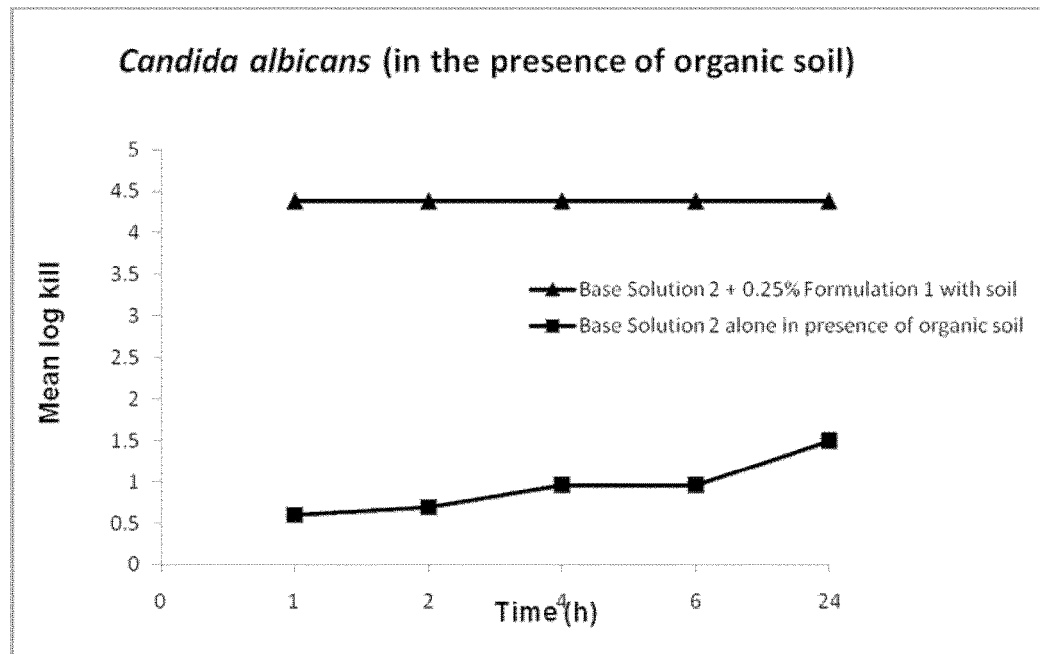
FIG. 7. The disinfecting effect of the addition of Formulation 1 to Contact Lens Solution 2 on a population of *Candida albicans* in the presence of organic soil.
Figure 10:
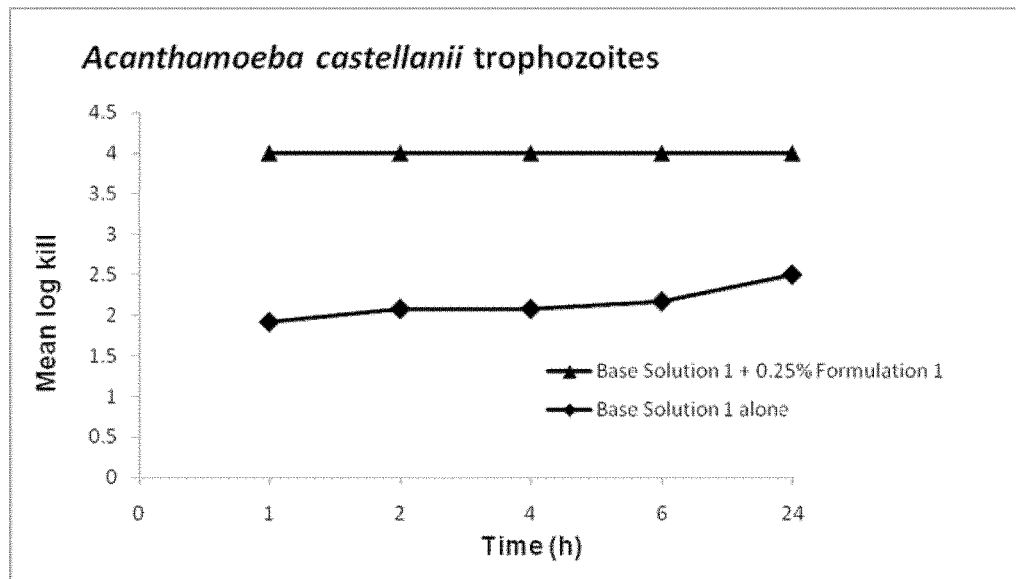
FIG. 10. The disinfecting effect of the addition of Formulation 1 to Contact Lens Solution 1 on a population of trophozoites of *Acanthamoeba castellanii*.
Figure 11:
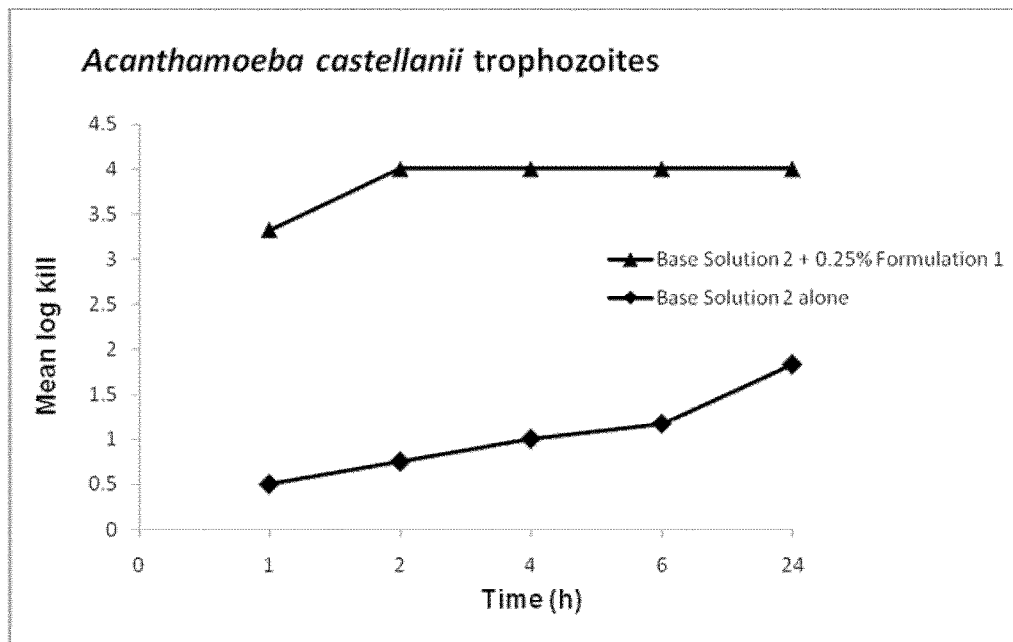
FIG. 11. The disinfecting effect of the addition of Formulation 1 to Contact Lens Solution 2 on a population of trophozoites of *Acanthamoeba castellanii*.
Figure 12:
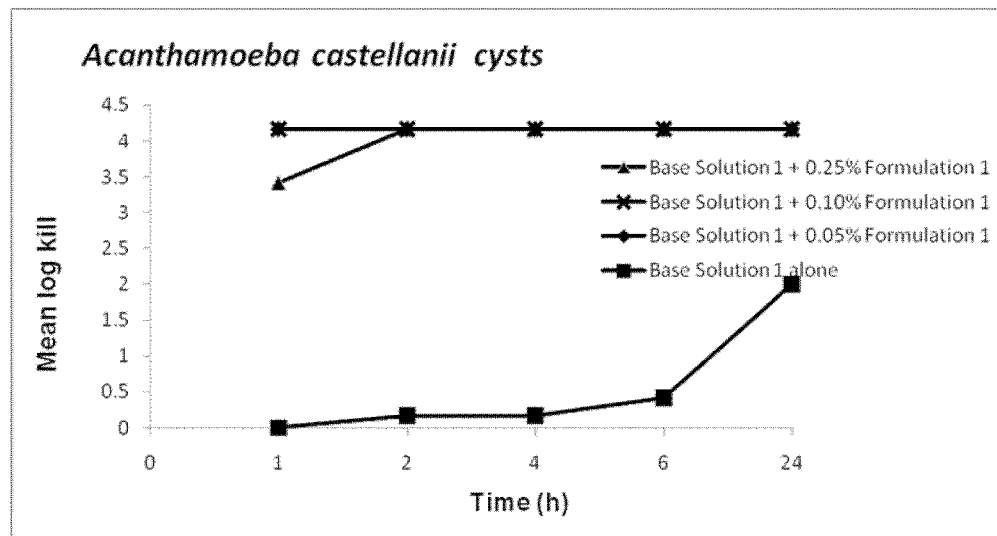
FIG. 12. The disinfecting effect of the addition of Formulation 1 to Contact Lens Solution 1 on a population of cysts of *Acanthamoeba castellanii*.
Figure 13:
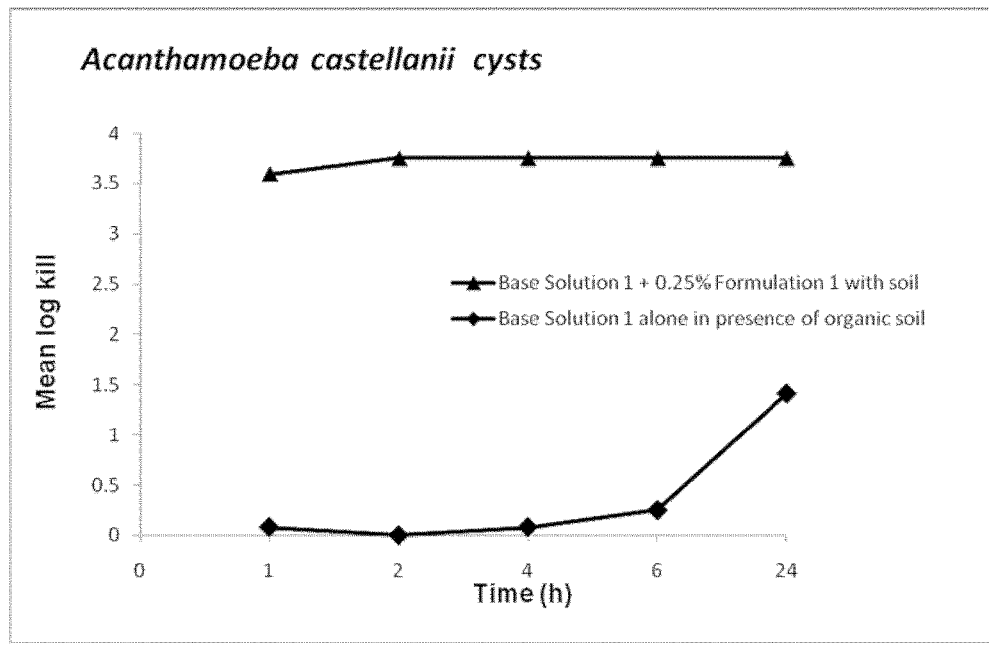
FIG. 13. The disinfecting effect of the addition of Formulation 1 to Contact Lens Solution 1 on a population of cysts of *Acanthamoeba castellanii* in the presence of organic soil.
Figure 14:
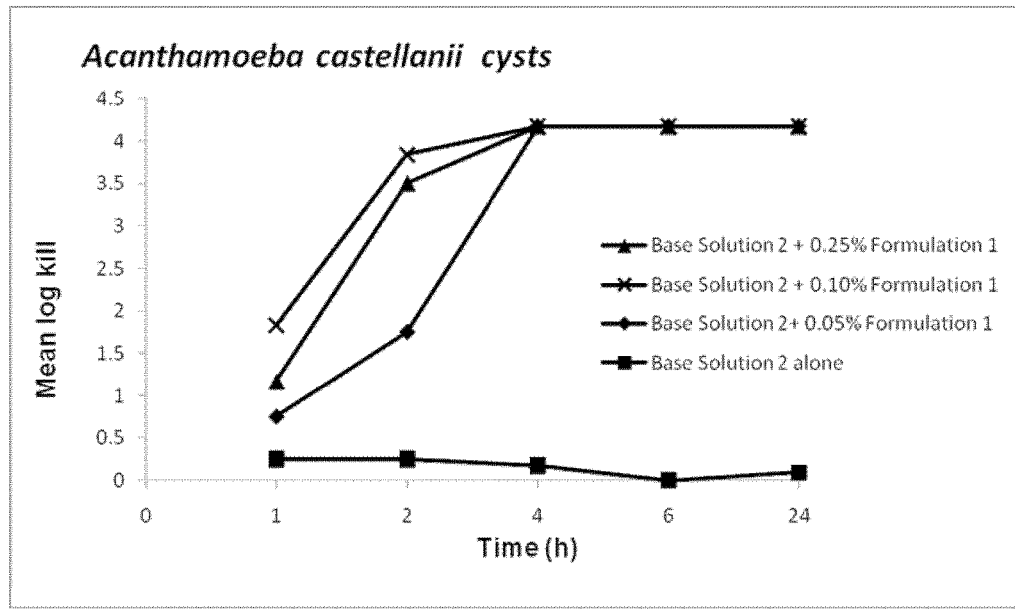
FIG. 14. The disinfecting effect of the addition of Formulation 1 to Contact Lens Solution 2 on a population of cysts of *Acanthamoeba castellanii*.
Figure 15:
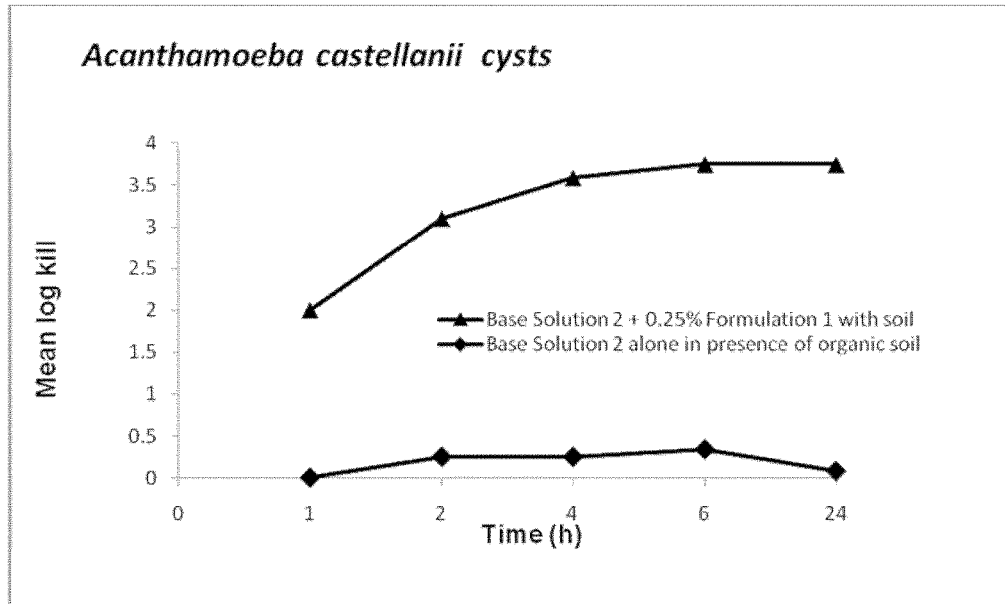
FIG. 15. The disinfecting effect of the addition of Formulation 1 to Contact Lens Solution 2 on a population of cysts of *Acanthamoeba castellanii* in the presence of organic soil.

The results are shown in Tables 17-32, and presented in FIGS. 1-15

TABLE 17

Results of *Staphylococcus aureus*, MRSA, blood stream infection with Base Solution 1

| Test solution | Time | Mean count/ml | Log count | Log kill | *SEM |
|---|---|---|---|---|---|
| Base Solution 1 | 0 hr | 480000 | 5.68 | 0.00 | 0.00 |
| | 1 hr | 10 | 1.00 | −4.68 | 0.00 |
| | 2 hr | 10 | 1.00 | −4.68 | 0.00 |
| | 4 hr | 10 | 1.00 | −4.68 | 0.00 |
| | 6 hr | 10 | 1.00 | −4.68 | 0.00 |
| | 24 hr | 10 | 1.00 | −4.68 | 0.00 |
| Base Solution 1 + | 0 hr | 480000 | 5.68 | 0.00 | 0.00 |
| 0.25% Formulation 1 | 1 hr | 10 | 1.00 | −4.68 | 0.00 |
| | 2 hr | 10 | 1.00 | −4.68 | 0.00 |
| | 4 hr | 10 | 1.00 | −4.68 | 0.00 |
| | 6 hr | 10 | 1.00 | −4.68 | 0.00 |
| | 24 hr | 10 | 1.00 | −4.68 | 0.00 |

TABLE 18

Results of *Staphylococcus aureus*, MRSA, blood stream infection with Base Solution 2

| Test solution | Time | Mean count/ml | Log count | Log kill | *SEM |
|---|---|---|---|---|---|
| Base Solution 2 | 0 hr | 480000 | 5.68 | 0.00 | 0.00 |
| | 1 hr | 783 | 2.89 | −2.79 | 0.02 |
| | 2 hr | 430 | 2.63 | −3.06 | 0.08 |
| | 4 hr | 100 | 2.00 | −3.69 | 0.06 |
| | 6 hr | 57 | 1.75 | −4.00 | 0.19 |
| | 24 hr | 20 | 1.30 | −4.42 | 0.14 |
| Base Solution 2 + | 0 hr | 480000 | 5.68 | 0.00 | 0.00 |
| 0.25% Formulation 1 | 1 hr | 10 | 1.00 | −4.68 | 0.00 |
| | 2 hr | 10 | 1.00 | −4.68 | 0.00 |
| | 4 hr | 10 | 1.00 | −4.68 | 0.00 |
| | 6 hr | 10 | 1.00 | −4.68 | 0.00 |
| | 24 hr | 10 | 1.00 | −4.68 | 0.00 |
| Base Solution 2 + | 0 hr | 356000 | 5.55 | 0.00 | 0.00 |
| 0.10% Formulation 1 | 1 hr | 10 | 1.00 | −4.55 | 0.00 |
| | 2 hr | 10 | 1.00 | −4.55 | 0.00 |
| | 4 hr | 10 | 1.00 | −4.55 | 0.00 |
| | 6 hr | 10 | 1.00 | −4.55 | 0.00 |
| | 24 hr | 10 | 1.00 | −4.55 | 0.00 |
| Base Solution 2 + | 0 hr | 356000 | 5.55 | 0.00 | 0.00 |
| 0.05% Formulation 1 | 1 hr | 10 | 1.00 | −4.55 | 0.00 |
| | 2 hr | 10 | 1.00 | −4.55 | 0.00 |
| | 4 hr | 10 | 1.00 | −4.55 | 0.00 |
| | 6 hr | 10 | 1.00 | −4.55 | 0.00 |
| | 24 hr | 10 | 1.00 | −4.55 | 0.00 |

TABLE 19

Results of *Staphylococcus aureus*, MRSA, blood stream infection with Base Solution 1 in the presence of 10% w/v organic soil

| Test solution | Time | Mean count/ml | Log count | Log kill | *SEM |
|---|---|---|---|---|---|
| Base Solution 1 + | 0 hr | 269099 | 5.43 | 0.00 | 0.00 |
| 10% organic soil | 1 hr | 400 | 2.60 | −2.87 | 0.14 |
| | 2 hr | 113 | 2.05 | −3.49 | 0.24 |
| | 4 hr | 10 | 1.00 | −4.43 | 0.00 |
| | 6 hr | 10 | 1.00 | −4.43 | 0.00 |
| | 24 hr | 10 | 1.00 | −4.43 | 0.00 |
| Base Solution 1 + | 0 hr | 269099 | 5.43 | 0.00 | 0.00 |
| 0.25% Formulation 1 + | 1 hr | 10 | 1.00 | −4.43 | 0.00 |
| 10% organic soil | 2 hr | 10 | 1.00 | −4.43 | 0.00 |
| | 4 hr | 10 | 1.00 | −4.43 | 0.00 |
| | 6 hr | 10 | 1.00 | −4.43 | 0.00 |
| | 24 hr | 10 | 1.00 | −4.43 | 0.00 |

TABLE 20

Results of *Staphylococcus aureus*, MRSA, blood stream infection with Base Solution 2 in the presence of 10% w/v rganic soil

| Test solution | Time | Mean count/ml | Log count | Log kill | *SEM |
|---|---|---|---|---|---|
| Base Solution 2 + | 0 hr | 269099 | 5.43 | 0.00 | 0.00 |
| 10% organic soil | 1 hr | 310 | 2.49 | −2.96 | 0.09 |
| | 2 hr | 90 | 1.95 | −3.49 | 0.07 |
| | 4 hr | 83 | 1.92 | −3.80 | 0.38 |
| | 6 hr | 10 | 1.00 | −4.43 | 0.00 |
| | 24 hr | 10 | 1.00 | −4.43 | 0.00 |
| Base Solution 2 + | 0 hr | 269099 | 5.43 | 0.00 | 0.00 |
| 0.25% Formulation 1 + | 1 hr | 10 | 1.00 | −4.43 | 0.00 |
| 10% organic soil | 2 hr | 10 | 1.00 | −4.43 | 0.00 |
| | 4 hr | 10 | 1.00 | −4.43 | 0.00 |
| | 6 hr | 10 | 1.00 | −4.43 | 0.00 |
| | 24 hr | 10 | 1.00 | −4.43 | 0.00 |

TABLE 21

Results of *Candida albicans*, ATCC 10231 with Base Solution 1

| Test solution | Time | Mean count/ml | Log count | Log kill | *SEM |
|---|---|---|---|---|---|
| Base Solution 1 | 0 hr | 605667 | 5.78 | 0.00 | 0.00 |
| | 1 hr | 32267 | 4.51 | −1.27 | 0.02 |
| | 2 hr | 21400 | 4.33 | −1.45 | 0.02 |
| | 4 hr | 13600 | 4.13 | −1.65 | 0.02 |
| | 6 hr | 8533 | 3.93 | −1.86 | 0.05 |
| | 24 hr | 10 | 1.00 | −4.78 | 0.00 |
| Base Solution 1 + 0.25% Formulation 1 | 0 hr | 605667 | 5.78 | 0.00 | 0.00 |
| | 1 hr | 10 | 1.00 | −4.78 | 0.00 |
| | 2 hr | 10 | 1.00 | −4.78 | 0.00 |
| | 4 hr | 10 | 1.00 | −4.78 | 0.00 |
| | 6 hr | 10 | 1.00 | −4.78 | 0.00 |
| | 24 hr | 10 | 1.00 | −4.78 | 0.00 |
| Base Solution 1 + 0.10% Formulation 1 | 0 hr | 664444 | 5.82 | 0.00 | 0.00 |
| | 1 hr | 10 | 1.00 | −4.82 | 0.00 |
| | 2 hr | 10 | 1.00 | −4.82 | 0.00 |
| | 4 hr | 10 | 1.00 | −4.82 | 0.00 |
| | 6 hr | 10 | 1.00 | −4.82 | 0.00 |
| | 24 hr | 10 | 1.00 | −4.82 | 0.00 |
| Base Solution 1 + 0.05% Formulation 1 | 0 hr | 664444 | 5.82 | 0.00 | 0.00 |
| | 1 hr | 10 | 1.00 | −4.82 | 0.00 |
| | 2 hr | 10 | 1.00 | −4.82 | 0.00 |
| | 4 hr | 10 | 1.00 | −4.82 | 0.00 |
| | 6 hr | 10 | 1.00 | −4.82 | 0.00 |
| | 24 hr | 10 | 1.00 | −4.82 | 0.00 |

TABLE 22

Results of *Candida albicans*, ATCC 10231 with Base Solution 2

| Test solution | Time | Mean count/ml | Log count | Log kill | *SEM |
|---|---|---|---|---|---|
| Base Solution 2 | 0 hr | 605667 | 5.78 | 0.00 | 0.00 |
| | 1 hr | 112327 | 5.05 | −0.74 | 0.04 |
| | 2 hr | 101796 | 5.01 | −0.81 | 0.12 |
| | 4 hr | 79206 | 4.90 | −0.90 | 0.07 |
| | 6 hr | 82284 | 4.92 | −0.88 | 0.07 |
| | 24 hr | 2810 | 3.45 | −2.34 | 0.04 |
| Base Solution 2 + 0.25% Formulation 1 | 0 hr | 605667 | 5.78 | 0.00 | 0.00 |
| | 1 hr | 10 | 1.00 | −4.78 | 0.00 |
| | 2 hr | 10 | 1.00 | −4.78 | 0.00 |
| | 4 hr | 10 | 1.00 | −4.78 | 0.00 |
| | 6 hr | 10 | 1.00 | −4.78 | 0.00 |
| | 24 hr | 10 | 1.00 | −4.78 | 0.00 |
| Base Solution 2 + 0.10% Formulation 1 | 0 hr | 664444 | 5.82 | 0.00 | 0.00 |
| | 1 hr | 10 | 1.00 | −4.82 | 0.00 |
| | 2 hr | 10 | 1.00 | −4.82 | 0.00 |
| | 4 hr | 10 | 1.00 | −4.82 | 0.00 |
| | 6 hr | 10 | 1.00 | −4.82 | 0.00 |
| | 24 hr | 10 | 1.00 | −4.82 | 0.00 |
| Base Solution 2 + 0.05% Formulation 1 | 0 hr | 664444 | 5.82 | 0.00 | 0.00 |
| | 1 hr | 533 | 2.73 | −3.16 | 0.18 |
| | 2 hr | 137 | 2.14 | −3.96 | 0.43 |
| | 4 hr | 10 | 1.00 | −4.82 | 0.00 |
| | 6 hr | 10 | 1.00 | −4.82 | 0.00 |
| | 24 hr | 10 | 1.00 | −4.82 | 0.00 |

TABLE 23

Results of *Candida albicans*, ATCC 10231 with Base Solution 1 in the presence of 10% w/v organic soil

| Test solution | Time | Mean count/ml | Log count | Log kill | *SEM |
|---|---|---|---|---|---|
| Base Solution 1 + 10% organic soil | 0 hr | 240063 | 5.38 | 0.00 | 0.00 |
| | 1 hr | 22000 | 4.34 | −1.04 | 0.05 |
| | 2 hr | 13200 | 4.12 | −1.26 | 0.03 |
| | 4 hr | 7400 | 3.87 | −1.51 | 0.02 |
| | 6 hr | 1867 | 3.27 | −2.13 | 0.10 |
| | 24 hr | 10 | 1.00 | −4.38 | 0.00 |
| Base Solution 1 + 0.25% Formulation 1 + 10% organic soil | 0 hr | 240063 | 5.38 | 0.00 | 0.00 |
| | 1 hr | 10 | 1.00 | −4.38 | 0.00 |
| | 2 hr | 10 | 1.00 | −4.38 | 0.00 |
| | 4 hr | 10 | 1.00 | −4.38 | 0.00 |
| | 6 hr | 10 | 1.00 | −4.38 | 0.00 |
| | 24 hr | 10 | 1.00 | −4.38 | 0.00 |

TABLE 24

Results of *Candida albicans*, ATCC 10231 with Base Solution 2 in the presence of 10% w/v organic soil

| Test solution | Time | Mean count/ml | Log count | Log kill | *SEM |
|---|---|---|---|---|---|
| Base Solution 2 + 10% organic soil | 0 hr | 240063 | 5.38 | 0.00 | 0.00 |
| | 1 hr | 65126 | 4.81 | −0.60 | 0.12 |
| | 2 hr | 51822 | 4.71 | −0.69 | 0.12 |
| | 4 hr | 26600 | 4.42 | −0.96 | 0.04 |
| | 6 hr | 26200 | 4.42 | −0.96 | 0.00 |
| | 24 hr | 7867 | 3.90 | −1.50 | 0.08 |
| Base Solution 2 + 0.25% Formulation 1 + 10% organic soil | 0 hr | 240063 | 5.38 | 0.00 | 0.00 |
| | 1 hr | 10 | 1.00 | −4.38 | 0.00 |
| | 2 hr | 10 | 1.00 | −4.38 | 0.00 |
| | 4 hr | 10 | 1.00 | −4.38 | 0.00 |
| | 6 hr | 10 | 1.00 | −4.38 | 0.00 |
| | 24 hr | 10 | 1.00 | −4.38 | 0.00 |

TABLE 25

Results of *Fusarium solani*, ATCC 36031 with Base Solution 1

| Test solution | Time | Mean count/ml | Log count | Log kill | *SEM |
|---|---|---|---|---|---|
| Base Solution 1 | 0 hr | 106667 | 5.03 | 0.00 | 0.00 |
| | 1 hr | 933 | 2.97 | −2.08 | 0.09 |
| | 2 hr | 373 | 2.57 | −2.60 | 0.25 |
| | 4 hr | 183 | 2.26 | −2.92 | 0.25 |
| | 6 hr | 70 | 1.85 | −3.23 | 0.16 |
| | 24 hr | 10 | 1.00 | −4.03 | 0.00 |
| Base Solution 1 + 0.25% Formulation 1 | 0 hr | 106667 | 5.03 | 0.00 | 0.00 |
| | 1 hr | 10 | 1.00 | −4.03 | 0.00 |
| | 2 hr | 10 | 1.00 | −4.03 | 0.00 |
| | 4 hr | 10 | 1.00 | −4.03 | 0.00 |
| | 6 hr | 10 | 1.00 | −4.03 | 0.00 |
| | 24 hr | 10 | 1.00 | −4.03 | 0.00 |

TABLE 26

Results of *Fusarium solani*, ATCC 36031 with Base Solution 2

| Test solution | Time | Mean count/ml | Log count | Log kill | *SEM |
|---|---|---|---|---|---|
| Base Solution 2 | 0 hr | 106667 | 5.03 | 0.00 | 0.00 |
| | 1 hr | 1200 | 3.08 | −1.95 | 0.00 |
| | 2 hr | 733 | 2.87 | −2.24 | 0.18 |
| | 4 hr | 167 | 2.22 | −2.81 | 0.01 |
| | 6 hr | 147 | 2.17 | −2.86 | 0.03 |
| | 24 hr | 10 | 1.00 | −4.03 | 0.00 |

TABLE 26-continued

Results of *Fusarium solani*, ATCC 36031 with Base Solution 2

| Test solution | Time | Mean count/ml | Log count | Log kill | *SEM |
|---|---|---|---|---|---|
| Base Solution 2 + | 0 hr | 106667 | 5.03 | 0.00 | 0.00 |
| 0.25% Formulation 1 | 1 hr | 10 | 1.00 | −4.03 | 0.00 |
| | 2 hr | 10 | 1.00 | −4.03 | 0.00 |
| | 4 hr | 10 | 1.00 | −4.03 | 0.00 |
| | 6 hr | 10 | 1.00 | −4.03 | 0.00 |
| | 24 hr | 10 | 1.00 | −4.03 | 0.00 |

TABLE 27

Results of *Acanthamoeba castellanii* (ATCC 50370) trophozoites with Base Solution 1

| Test solution | Time | Mean count/ml | Log count | Log kill | *SEM |
|---|---|---|---|---|---|
| Base Solution 1 | 0 | 11200 | 4.05 | 0.00 | 0.00 |
| | 1 | 127 | 2.10 | −1.92 | 0.08 |
| | 2 | 97 | 1.99 | −2.08 | 0.30 |
| | 4 | 97 | 1.99 | −2.08 | 0.30 |
| | 6 | 71 | 1.85 | −2.17 | 0.17 |
| | 24 | 32 | 1.51 | −2.50 | 0.15 |
| Base Solution 1 + | 0 | 11200 | 4.05 | 0.00 | 0.00 |
| 0.25% Formulation 1 | 1 | 0 | 0.00 | −4.00 | 0.15 |
| | 2 | 0 | 0.00 | −4.00 | 0.15 |
| | 4 | 0 | 0.00 | −4.00 | 0.15 |
| | 6 | 0 | 0.00 | −4.00 | 0.15 |
| | 24 | 0 | 0.00 | −4.00 | 0.15 |

TABLE 28

Results of *Acanthamoeba castellanii* (ATCC 50370) trophozoites with Base Solution 2

| Test solution | Time | Mean count/ml | Log count | Log kill | *SEM |
|---|---|---|---|---|---|
| Base Solution 2 | 0 | 11200 | 4.05 | 0.00 | 0.00 |
| | 1 | 3533 | 3.55 | −0.50 | 0.14 |
| | 2 | 1800 | 3.26 | −0.75 | 0.15 |
| | 4 | 1120 | 3.05 | −1.00 | 0.25 |
| | 6 | 773 | 2.89 | −1.17 | 0.30 |
| | 24 | 257 | 2.41 | −1.83 | 0.46 |
| Base Solution 2 + | 0 | 11200 | 4.05 | 0.00 | 0.00 |
| 0.25% Formulation 1 | 1 | 8 | 0.92 | −3.32 | 0.22 |
| | 2 | 0 | 0.00 | −4.00 | 0.15 |
| | 4 | 0 | 0.00 | −4.00 | 0.15 |
| | 6 | 0 | 0.00 | −4.00 | 0.15 |
| | 24 | 0 | 0.00 | −4.00 | 0.15 |

TABLE 29

Results of *Acanthamoeba castellanii* (ATCC 50370) cysts with Base Solution 1

| Test solution | Time | Mean count/ml | Log count | Log kill | *SEM |
|---|---|---|---|---|---|
| Base Solution 1 | 0 | 15333 | 4.19 | 0.00 | 0.00 |
| | 1 | 22667 | 4.36 | 0.17 | 0.08 |
| | 2 | 15067 | 4.18 | −0.17 | 0.37 |
| | 4 | 11200 | 4.05 | −0.17 | 0.17 |
| | 6 | 8467 | 3.93 | −0.42 | 0.37 |
| | 24 | 173 | 2.24 | −2.00 | 0.15 |
| Base Solution 1 + | 0 | 15333 | 4.19 | 0.00 | 0.00 |
| 0.25% Formulation 1 | 1 | 10 | 0.99 | −3.42 | 0.30 |
| | 2 | 0 | 0.00 | −4.17 | 0.09 |
| | 4 | 0 | 0.00 | −4.17 | 0.09 |
| | 6 | 0 | 0.00 | −4.17 | 0.09 |
| | 24 | 0 | 0.00 | −4.17 | 0.09 |
| Base Solution 1 + | 0 | 18533 | 4.27 | 0.00 | 0.00 |
| 0.10% Formulation 1 | 1 | 0 | 0.00 | −4.17 | 0.22 |
| | 2 | 0 | 0.00 | −4.17 | 0.22 |
| | 4 | 0 | 0.00 | −4.17 | 0.22 |
| | 6 | 0 | 0.00 | −4.17 | 0.22 |
| | 24 | 0 | 0.00 | −4.17 | 0.22 |
| Base Solution 1 + | 0 | 18533 | 4.27 | 0.00 | 0.00 |
| 0.05% Formulation 1 | 1 | 0 | 0.00 | −4.17 | 0.22 |
| | 2 | 0 | 0.00 | −4.17 | 0.22 |
| | 4 | 0 | 0.00 | −4.17 | 0.22 |
| | 6 | 0 | 0.00 | −4.17 | 0.22 |
| | 24 | 0 | 0.00 | −4.17 | 0.22 |

TABLE 30

Results of *Acanthamoeba castellanii* (ATCC 50370) cysts with Base Solution 2

| Test solution | Time | Mean count/ml | Log count | Log kill | *SEM |
|---|---|---|---|---|---|
| Base Solution 2 | 0 | 15333 | 4.19 | 0.00 | 0.00 |
| | 1 | 9733 | 3.99 | −0.25 | 0.25 |
| | 2 | 13600 | 4.13 | −0.25 | 0.38 |
| | 4 | 11200 | 4.05 | −0.17 | 0.08 |
| | 6 | 17333 | 4.24 | 0.00 | 0.25 |
| | 24 | 15867 | 4.20 | −0.09 | 0.17 |
| Base Solution 2 + | 0 | 15333 | 4.19 | 0.00 | 0.00 |
| 0.25% Formulation 1 | 1 | 1000 | 3.00 | −1.17 | 0.09 |
| | 2 | 7 | 0.85 | −3.50 | 0.38 |
| | 4 | 0 | 0.00 | −4.17 | 0.09 |
| | 6 | 0 | 0.00 | −4.17 | 0.09 |
| | 24 | 0 | 0.00 | −4.17 | 0.09 |
| Base Solution 2 + | 0 | 18533 | 4.27 | 0.00 | 0.00 |
| 0.10% Formulation 1 | 1 | 227 | 2.36 | −1.83 | 0.30 |
| | 2 | 4 | 0.60 | −3.84 | 0.22 |
| | 4 | 0 | 0.00 | −4.17 | 0.22 |
| | 6 | 0 | 0.00 | −4.17 | 0.22 |
| | 24 | 0 | 0.00 | −4.17 | 0.22 |
| Base Solution 2 + | 0 | 18533 | 4.27 | 0.00 | 0.00 |
| 0.05% Formulation 1 | 1 | 2733 | 3.44 | −0.75 | 0.15 |
| | 2 | 273 | 2.44 | −1.75 | 0.29 |
| | 4 | 0 | 0.00 | −4.17 | 0.22 |
| | 6 | 0 | 0.00 | −4.17 | 0.22 |
| | 24 | 0 | 0.00 | −4.17 | 0.22 |

TABLE 31

Results of *Acanthamoeba castellanii* (ATCC 50370) cysts with Base Solution 1 in the presence of 10% w/v organic soil

| Test solution | Time (hr) | Mean count/ml | Mean log count | Mean log kill | SEM* |
|---|---|---|---|---|---|
| Base Solution 1 + | 0 | 5600 | 3.75 | 0.00 | 0.00 |
| 10% organic soil | 1 | 4800 | 3.68 | −0.08 | 0.08 |
| | 2 | 7267 | 3.86 | 0.00 | 0.25 |
| | 4 | 4800 | 3.68 | −0.08 | 0.08 |
| | 6 | 3533 | 3.55 | −0.25 | 0.14 |
| | 24 | 247 | 2.39 | −1.41 | 0.17 |

TABLE 31-continued

Results of *Acanthamoeba castellanii* (ATCC 50370) cysts with Base Solution 1 in the presence of 10% w/v organic soil

| Test solution | Time (hr) | Mean count/ml | Mean log count | Mean log kill | SEM* |
|---|---|---|---|---|---|
| Base Solution 1 + | 0 | 5600 | 3.75 | 0.00 | 0.00 |
| 0.25% Formulation 1 + | 1 | 2 | 0.22 | −3.59 | 0.16 |
| 10% organic soil | 2 | 0 | 0.00 | −3.75 | 0.00 |
|  | 4 | 0 | 0.00 | −3.75 | 0.00 |
|  | 6 | 0 | 0.00 | −3.75 | 0.00 |
|  | 24 | 0 | 0.00 | −3.75 | 0.00 |

TABLE 32

Results of *Acanthamoeba castellanii* (ATCC 50370) cysts with Base Solution 2 in the presence of 10% w/v organic soil

| Test solution | Time (hr) | Mean count/ml | Mean log count | Mean log kill | SEM* |
|---|---|---|---|---|---|
| Base Solution 2 + | 0 | 5600 | 3.75 | 0.00 | 0.00 |
| 10% organic soil | 1 | 6267 | 3.80 | 0.00 | 0.14 |
|  | 2 | 11200 | 4.05 | 0.25 | 0.15 |
|  | 4 | 11200 | 4.05 | 0.25 | 0.15 |
|  | 6 | 12667 | 4.10 | 0.34 | 0.09 |
|  | 24 | 7067 | 3.85 | 0.08 | 0.08 |
| Base Solution 2 + | 0 | 5600 | 3.75 | 0.00 | 0.00 |
| 0.25% | 1 | 56 | 1.75 | −2.00 | 0.00 |
| Formulation 1 + | 2 | 5 | 0.73 | −3.10 | 0.17 |
| 10% organic soil | 4 | 2 | 0.22 | −3.59 | 0.16 |
|  | 6 | 0 | 0.00 | −3.75 | 0.00 |
|  | 24 | 0 | 0.00 | −3.75 | 0.00 |

In summary, from these Tables it may be concluded that the addition of the Formulation 1 to standard contact lens solutions enhances the anti-microbial activity against *Staphylococcus aureus*, *Candida albicans*, *Fusarium solani* and *Acanthamoeba castellanii* (trophozoites and cysts).

Example 8—Contact Lens Compatibility

Formulation 4 diluted to 0.5% v/v with 0.9% w/v saline was tested for contact lens compatibility. It was found that for the rigid gas permeable material assessed—Optimum Comfort—the lenses did not appear to have displayed any changes of note compared to the control lenses. This is observed for the lenses in three power groups. The effect of the solution on traditional soft hydrophilic lenses was investigated by use of both low water content (CF38%) and high water content (IG67%) materials. The CF38 material is a typical poly(HEMA) product (FDA classification as polymacon) and a version with a blue handling tint was used for this study. No significant changes in lens parameters were recorded for the test lenses compared to the control lenses for any of the three power groups investigated. The IG67 material is typical of a traditional high water content material and uses vinyl pyrrolidone as the main hydrophilic component. Again no significant differences in lens parameters for all three power groups with exposure to the test solution was observed compared to control lenses. For the Definitive silicone hydrogel lenses, no significant changes were observed for lenses in each of the power groups.

Example 9—Preservative Efficacy Testing of Formulations 3 and 4

Prior to the test, the micro-organisms are cultured on media appropriate for the organism and harvested to afford culture suspensions at around $10^8$ cfu/ml. A sample of each suspension is removed and serially diluted for enumeration and validation controls.

For each of the test samples, 10 ml was dispensed into a glass universal for each organism. A blank control was also initiated for each organism. The micro-organisms suspensions ($10^8$ cfu/ml, 0.1 ml) were added to the universals and the product mixed to ensure homogeneity. Controls were performed using a 1:100 dilution of the product in broth, as well as blank broth which were then spiked with a low level spike of organism and plated out to ensure adequate neutralisation of any preservatives.

The solutions of inoculated product were incubated at 20-25° C. in the absence of light. At the time-points relevant to the organism under test (0, 6 h, 24 h, 7 day, 28 day for bacteria and 0, 7, 14 and 28 days for yeast and moulds), a sample (1 ml) was removed, diluted as appropriate and plated out to determine the number of viable micro-organisms. The $\log_{10}$ reduction was calculated from the inoculum levels and the final recovery level of the organism, compensating for any dilutions performed during testing.

The number of viable micro-organisms in the culture suspensions are given in Table 33.

TABLE 33

Viable counts of culture suspensions

| Organism | Count ($\log_{10}$ cfu/ml) |
|---|---|
| *Aspergillus niger* | 7.6 |
| *Candida albicans* | 7.8 |
| *Zygosachharomyces rouxii* | 7.7 |
| *Pseudomonas aeruginosa* | 7.6 |
| *Staphylococcus aureus* | 8.0 |
| *Escherichia coli* | 8.1 |

The recovery counts for the low level spiked controls all passed the validation criteria.

The recovery counts at the specific time-points for 0.5% Formulation 3, 1% Formulation 3, 0.5% Formulation 4 and 1% Formulation 4 are given in Tables 34, 35, 36 and 37 respectively.

TABLE 34

Recovery counts after incubation with 0.5% v/v Formulation 3

| Organism | $\log_{10}$ recovery 0 h | $\log_{10}$ reduction 6 h | 24 h | 7 day | 14 day | 28 day |
|---|---|---|---|---|---|---|
| *A. niger* | 5.3 | nd | nd | 1.0 | 1.0 | 1.2 |
| *C. albicans* | >5.5 | nd | nd | 3.7 | >4.8 | >4.8 |
| *Z. rouxii* | >5.5 | nd | nd | >4.7 | >4.7 | >4.7 |
| *P. aeruginosa* | 5.2 | 2.4 | >4.7 | >4.7 | nd | >4.7 |
| *S. aureus* | 4.8 | >5.0 | >5.0 | >5.0 | nd | >5.0 |
| *E. coli* | >5.5 | >5.1 | >5.1 | >5.1 | nd | >5.1 | nd = not determined

TABLE 35

Recovery counts after incubation with 1.0% v/v Formulation 3

| Organism | log₁₀ recovery 0 h | Log₁₀ reduction | | | | |
|---|---|---|---|---|---|---|
| | | 6 h | 24 h | 7 day | 14 day | 28 day |
| A. niger | 5.1 | nd | nd | 1.8 | 2.1 | 2.2 |
| C. albicans | 5.4 | nd | nd | >4.8 | >4.8 | >4.8 |
| Z. rouxii | >5.5 | nd | nd | >4.7 | >4.7 | >4.7 |
| P. aeruginosa | 5.3 | >4.7 | >4.7 | >4.7 | nd | >4.7 |
| S. aureus | 3.7 | >5.0 | >5.0 | >5.0 | nd | >5.0 |
| E. coli | 5.4 | >5.1 | >5.1 | >5.1 | nd | >5.1 | nd = not determined

TABLE 36

Recovery counts after incubation with 0.5% v/v Formulation 4

| Organism | log₁₀ recovery 0 h | Log₁₀ reduction | | | | |
|---|---|---|---|---|---|---|
| | | 6 h | 24 h | 7 day | 14 day | 28 day |
| A. niger | 5.0 | nd | nd | >4.6 | >4.6 | >4.6 |
| C. albicans | 5.5 | nd | nd | >4.8 | >4.8 | >4.8 |
| Z. rouxii | 5.1 | nd | nd | >4.7 | >4.7 | >4.7 |
| P. aeruginosa | 4.5 | >4.7 | >4.7 | >4.7 | nd | >4.7 |
| S. aureus | <1 | >5.0 | >5.0 | >5.0 | nd | >5.0 |
| E. coli | 4.9 | >5.1 | >5.1 | >5.1 | nd | >5.1 | nd = not determined

TABLE 37

Recovery counts after incubation with 1% v/v Formulation 4

| Organism | log₁₀ recovery 0 h | Log₁₀ reduction | | | | |
|---|---|---|---|---|---|---|
| | | 6 h | 24 h | 7 day | 14 day | 28 day |
| A. niger | 4.9 | nd | nd | 4.6 | 4.6 | >4.6 |
| C. albicans | 5.2 | nd | nd | >4.8 | >4.8 | >4.8 |
| Z. rouxii | 4.8 | nd | nd | >4.7 | >4.7 | >4.7 |
| P. aeruginosa | 4.8 | >4.7 | >4.7 | >4.7 | nd | >4.7 |
| S. aureus | 2.1 | >5.0 | >5.0 | >5.0 | nd | >5.0 |
| E. coli | 4.9 | >5.1 | >5.1 | >5.1 | nd | >5.1 | nd = not determined

It was found that both Formulation 3 and 4 at 0.5 and 1.0% w/v are effective antimicrobial preservatives.

Example 10—Ocular Tolerance in Rabbits

Following multiple instillations of Formulation 3 at either (a) 3% v/v or (b) 1% v/v or (c) 2% v/v dilutions with 0.9% saline in the right eye of albino rabbits for 6 days, no significant ocular reactions were observed. The 1% concentration appeared to be slightly more irritant than the other two concentrations or vehicle alone. However, because there was clearly no dose-dependant findings and the untreated eyes showed similar findings, this apparent difference is not considered significant or clinically significant.

Therefore, in these experimental conditions, Formulation 3 was macroscopically very well tolerated at 1%, 2% and 3% v/v concentrations.

Unless indicated to the contrary, % values as used herein are % w/w values.

The foregoing broadly describes the present invention, without limitation. Variations and modifications as will be readily apparent to those of ordinary skill in this art are intended to be included within the scope of this application and subsequent patents.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and suitable and more suitable groups and embodiments of groups recited above.

The invention claimed is:

1. A method of storing and disinfecting a contact lens, the method comprising bringing said contact lens into contact with a contact lens solution for a sufficient duration to disinfect said contact lens,
   wherein the contact lens solution comprises effective amounts of:
   an extract from the pith of immature bitter oranges (*Citrus aurantium*) which contains the bioflavonoids naringin and neohesperidin;
   a fruit acid selected from the group consisting of malic acid, ascorbic acid, citric acid, tartaric acid, and a mixture thereof; and
   one or both of an aqueous antimicrobial contact lens storage composition agent and a disinfection composition agent.

2. The method according to claim 1, wherein the method comprises bringing said contact lens into contact with said contact lens solution for at least 1 hour.

3. The method according to claim 1, wherein said contact lens is disinfected with respect to actual or potential colonization by one or more microorganisms selected from the group consisting of *Acanthamoeba* sp, *Aspergillus niger, Bacillus cereus, Clostridium difficile, Staphylococcus aureus, Pseudomonas aeruginosa, Staphylococcus epidermidis*, methicillin resistant *Staphylococcus aureus* (MRSA) and *Fusarium solani*.

4. The method according to claim 1, wherein said contact lens is disinfected with respect to actual or potential presence of one or both of *Acanthamoeba* sp. trophozoites and cysts.

5. The method according to claim 1, wherein the contact lens solution further comprises other bioflavonoids.

6. The method according to claim 1, wherein the naringin and neohesperidin comprise in excess of 75% of bioflavonoids present.

7. The method according to claim 1, wherein the contact lens solution comprises an ophthalmic adjuvant component selected from the group consisting of: a buffer; a viscosity inducing component and a tonicity component comprising about 0.1% to 1.0% of sodium chloride; and a combination thereof.

8. The method according to claim 1, wherein the contact lens solution has a pH between 5 and 8.

9. The method of claim 1, wherein the contact lens solution is comprises both the aqueous antimicrobial contact lens storage agent and the disinfection agent.

10. The method of claim 1, wherein the at least one bioflavonoid comprises the mixture of narangin, neohesperidin and other bioflavonoids, and the fruit acid comprises malic acid, citric acid, and ascorbic acid.

11. The method of claim 10, wherein the lens solution further comprises choline hydroxide, glycerine, and an alkyl polyglucoside.

\* \* \* \* \*